(12) United States Patent
Lin et al.

(10) Patent No.: US 9,878,010 B2
(45) Date of Patent: Jan. 30, 2018

(54) METHODS OF TREATING METABOLIC DISORDERS

(71) Applicant: THE REGENTS OF THE UNIVERSITY OF MICHIGAN, Ann Arbor, MI (US)

(72) Inventors: Jiandie Lin, Ann Arbor, MI (US); Guoxiao Wang, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/778,379

(22) PCT Filed: Mar. 19, 2014

(86) PCT No.: PCT/US2014/031171
§ 371 (c)(1),
(2) Date: Sep. 18, 2015

(87) PCT Pub. No.: WO2014/153385
PCT Pub. Date: Sep. 25, 2014

(65) Prior Publication Data
US 2016/0279201 A1   Sep. 29, 2016

Related U.S. Application Data

(60) Provisional application No. 61/804,046, filed on Mar. 21, 2013.

(51) Int. Cl.
*A61K 38/00* (2006.01)
*A61K 38/18* (2006.01)
*G01N 33/68* (2006.01)
*A61K 45/06* (2006.01)

(52) U.S. Cl.
CPC .......... *A61K 38/1883* (2013.01); *A61K 45/06* (2013.01); *G01N 33/6893* (2013.01); *G01N 2333/475* (2013.01); *G01N 2800/04* (2013.01); *G01N 2800/042* (2013.01); *G01N 2800/044* (2013.01)

(58) Field of Classification Search
None
See application file for complete search history.

(56) References Cited

U.S. PATENT DOCUMENTS

| | | |
|---|---|---|
| 4,366,241 A | 12/1982 | Tom et al. |
| 4,376,110 A | 3/1983 | David et al. |
| 4,517,288 A | 5/1985 | Giegel et al. |
| 4,837,168 A | 6/1989 | de Jaeger et al. |
| 2004/0005622 A1* | 1/2004 | Schleyer ............ C07K 14/4756 435/6.14 |
| 2004/0121326 A1 | 6/2004 | Harari et al. |
| 2007/0015839 A1 | 1/2007 | Folli et al. |

FOREIGN PATENT DOCUMENTS

| | | | |
|---|---|---|---|
| WO | WO-2001/081540 A2 | | 11/2001 |
| WO | WO 2008/006922 | * | 1/2008 |
| WO | WO-2008/006922 A1 | | 1/2008 |
| WO | WO-2010/138387 A2 | | 12/2010 |
| WO | WO-2012/154987 A1 | | 11/2012 |

OTHER PUBLICATIONS

Sequence Listing of WO 2008/006922 (Jan. 2008).*
Blobel et al., The role of protease activity in ErbB biology. *Exp. Cell Res.* 315: 671-82 (2009).
Browning et al. Prevalence of hepatic steatosis in an urban population in the United States: Impact of ethnicity. *Hepatology* 40: 1387-95 (2004).
Burgess et al., EGFR family: structure physiology signalling and therapeutic targets. *Growth Factors* 26: 263-74 (2008).
Chitturi et al., NASH and insulin resistance: Insulin hypersecretion and specific association with the insulin resistance syndrome. *Hepatology* 35: 373-9 (2002).
Cohen et al., Human fatty liver disease: Old questions and new insights. *Science* 332: 1519-23 (2011).
Dunn et al., Co-expression of neuregulins 1, 2, 3 and 4 in human breast cancer. *J. Pathol.* 203: 672-80 (2004).
Ebi et al., The role of neuregulin4 and HER4 in gastrointestinal malignant lymphoma. *Molec. Med. Reports* 4: 1151-5 (2011).
Falls, Neuregulins and the neuromuscular system: 10 years of answers and questions. *J. Neurocytol.* 32: 619-47 (2003).
Falls, Neuregulins: Functions, forms, and signaling strategies. *Exp. Cell Res.* 284: 14-30 (2003).
Harari et al., Neuregulin-4: a novel growth factor that acts through the ErbB-4 receptor tyrosine kinase. *Oncogene* 18: 2681-9 (1999).
Hayes et al., Identification and characterization of novel spliced variants of neuregulin 4 in prostate cancer. *Clin. Cancer Res.* 13: 3147-55 (2007).
Hayes et al., Characterization of the cell membrane-associated products of the Neuregulin 4 gene. *Oncogene* 27: 715-20 (2008).
James et al., Non-alcoholic steatohepatitis: another disease of affluence. *Lancet* 353: 1634-6 (1999).
Jornayvaz et al., The role of muscle insulin resistance in the pathogenesis of atherogenic dyslipidemia and nonalcoholic fatty liver disease associated with the metabolic syndrome. *Annu. Rev. Nutr.* 30: 273-90 (2010).
Li et al., Genome-wide coactivation analysis of PGC-1alpha identifies BAF60a as a regulator of hepatic lipid metabolism. *Cell Metab.* 8: 105-17 (2008).
Lin et al., Induction of megakaryocyte differentiation by a novel pregnancy-specific hormone. *J. Biol. Chem.* 274: 21485-9 (1999).
Loomba et al., Advances in pediatric nonalcoholic fatty liver disease. *Hepatology*, 50: 1282-93 (2009).
Muller et al., Placental lactogen-I (PL-I) target tissues identified with an alkaline phosphatase-PL-I fusion protein. *J. Histochem. Cytochem.* 46: 737-43 (1998).

(Continued)

*Primary Examiner* — Jeanette Lieb
(74) *Attorney, Agent, or Firm* — Marshall, Gerstein & Borun LLP

(57) ABSTRACT

Methods of treating metabolic and/or lipid disorders are provided comprising administering to a patient in need thereof a therapeutically effective amount of Nrg4, an Nrg4 variant, or a biologically active fragment thereof.

14 Claims, 25 Drawing Sheets

(56) References Cited

OTHER PUBLICATIONS

Figure 1:
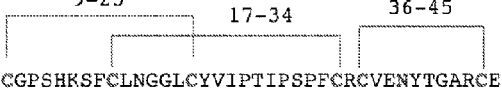

Reiss et al., The "A disintegrin and metalloprotease" (ADAM) family of sheddases: Physiological and cellular functions. *Sem. Cell Develop. Biol.* 20: 126-37 (2009).
Schneider et al., The epidermal growth factor receptor ligands at a glance. *J. Cell. Physiol.* 218: 460-6 (2009).
Stefansson et al., Neuregulin 1 and susceptibility to schizophrenia. *Am.J. Human Genet.* 71: 877-92 (2002).
Sung et al., Adipose vascular endothelial growth factor regulates metabolic homeostasis through angiogenesis. *Cell Metab.* 17: 61-72 (2013).
Szczepaniak et al., Magnetic resonance spectroscopy to measure hepatic triglyceride content: prevalence of hepatic steatosis in the general population. *Am. J. Physiol. Endocrinol. Metab.* 288: E462-8 (2005).
Tang et al., Genome-wide copy number analysis uncovers a new HSCR gene: NRG3. *PLoS Genet.* 8: e1002687 (2012).
International Search Report and Written Opinion of the International Searching Authority issued in connection with International Application No. PCT/US2014/031171, United States Patent and Trademark Office (ISA/US), dated Aug. 29, 2014.

\* cited by examiner

SEQUENCE LISTING

```
<160> NUMBER OF SEQ ID NOS: 5

<210> SEQ ID NO 1
<211> LENGTH: 115
<212> TYPE: PRT
<213> ORGANISM: Homo sapiens

<400> SEQUENCE: 1

Met Pro Thr Asp His Glu Glu Pro Cys Gly Pro Ser His Lys Ser Phe
1               5                   10                  15

Cys Leu Asn Gly Gly Leu Cys Tyr Val Ile Pro Thr Ile Pro Ser Pro
            20                  25                  30

Phe Cys Arg Cys Val Glu Asn Tyr Thr Gly Ala Arg Cys Glu Glu Val
        35                  40                  45

Phe Leu Pro Gly Ser Ser Ile Gln Thr Lys Ser Asn Leu Phe Glu Ala
    50                  55                  60

Phe Val Ala Leu Ala Val Leu Val Thr Leu Ile Ile Gly Ala Phe Tyr
65                  70                  75                  80

Phe Leu Cys Arg Lys Gly His Phe Gln Arg Ala Ser Ser Val Gln Tyr
                85                  90                  95

Asp Ile Asn Leu Val Glu Thr Ser Ser Thr Ser Ala His His Ser His
            100                 105                 110

Glu Gln His
        115

<210> SEQ ID NO 2
<211> LENGTH: 115
<212> TYPE: PRT
<213> ORGANISM: Mus musculus

<400> SEQUENCE: 2

Met Pro Thr Asp His Glu Gln Pro Cys Gly Pro Arg His Arg Ser Phe
1               5                   10                  15

Cys Leu Asn Gly Gly Ile Cys Tyr Val Ile Pro Thr Ile Pro Ser Pro
            20                  25                  30

Phe Cys Arg Cys Ile Glu Asn Tyr Thr Gly Ala Arg Cys Glu Glu Val
        35                  40                  45

Phe Leu Pro Ser Ser Ser Ile Pro Ser Glu Ser Asn Leu Ser Ala Ala
    50                  55                  60

Phe Val Val Leu Ala Val Leu Leu Thr Leu Thr Ile Ala Ala Leu Cys
65                  70                  75                  80

Phe Leu Cys Arg Lys Gly His Leu Gln Arg Ala Ser Ser Val Gln Cys
                85                  90                  95

Glu Ile Ser Leu Val Glu Thr Asn Asn Thr Arg Thr Arg His Ser His
            100                 105                 110

Arg Glu His
        115

<210> SEQ ID NO 3
<211> LENGTH: 20
<212> TYPE: DNA
```

```
<213> ORGANISM: Artificial Sequence
<220> FEATURE:
<223> OTHER INFORMATION: Synthetic primer

<400> SEQUENCE: 3
cccagcccat tctgtaggtg                                          20

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
accacgaaag ctgccgacag                                          20

<210> SEQ ID NO 5
<211> LENGTH: 22
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: 5' 6-FAM
<220> FEATURE:
<221> NAME/KEY: misc_feature
<222> LOCATION: (22)..(22)
<223> OTHER INFORMATION: 3' BHQ

<400> SEQUENCE: 5
cggagcacgc tgcgaagagg tt                                       22
```

METHODS OF TREATING METABOLIC DISORDERS

GOVERNMENT SUPPORT

This invention was made with government support under Grant Nos. HL097738 and DK077086 awarded by the National Institutes of Health. The government has certain rights in the invention.

INCORPORATION BY REFERENCE OF MATERIAL SUBMITTED ELECTRONICALLY

This application contains, as a separate part of the disclosure, a Sequence Listing in computer-readable form (filename: 46768S_SeqListing.txt; created Mar. 18, 2014, 3,026 byte—ASCII text file) which is incorporated by reference in its entirety.

FIELD OF THE INVENTION

The invention relates to methods of treating conditions characterized by Neuregulin 4 (Nrg4) deficiency, such as metabolic disorders.

BACKGROUND

Metabolic syndrome has become a global epidemic that dramatically increases the risk for type 2 diabetes, cardiovascular disease, and non-alcoholic fatty liver disease (NAFLD). Elevated hepatic glucose production and lipoprotein secretion contribute to the pathogenesis of hyperglycemia and hyperlipidemia in insulin resistance. Obesity is also associated with excess fat accumulation in the liver, a defining feature of NAFLD that affects both adults and children. While hepatic steatosis often exists as a benign condition with no apparent adverse effects on liver function, progressive liver injury, inflammation, and fibrosis are observed in 20-30% of NAFLD patients with non-alcoholic steatohepatitis (NASH). NASH is emerging as a major risk factor for end-stage liver diseases. The regulatory networks that control hepatic glucose and lipid metabolism have been the focus of research in the past two decades. These studies provide critical insights into the molecular and physiological mechanisms that contribute to glucose and lipid homeostasis. However, hormonal cues that mediate the crosstalk among different tissues, particularly between adipose tissues and the liver, remain poorly defined.

Neuregulins (NRGs) are a family of growth factors that contains a conserved epidermal growth factor (EGF)-like domain. To date, four neuregulin genes (Nrg1-4) have been identified in mammals that generate a diverse array of signaling ligands through extensive alternative splicing. NRGs are typically synthesized as transmembrane proteins that undergo proteolytic cleavage to liberate the extracellular fragments containing the EGF-like domain. Genetic and biochemical studies have demonstrated that NRGs signal through the ErbB family of tyrosine kinase receptors and exert their biological effects in a paracrine, autocrine, and endocrine manner. Nrg1 has been extensively characterized in the development of neuromuscular system, particularly the neuromuscular synapse and the peripheral nerve. In addition, Nrg1 plays an important role in the maintenance of cardiac homeostasis and central nervous system development. Genetic polymorphisms of Nrg1 and Nrg3 have been associated with the risk for schizophrenia and Hirschsprung Disease, respectively. NRGs elicit surprisingly specific biological response in target cells. Nrg4 was discovered based on its sequence homology to other NRG members and was predicted to encode a precursor protein of 115 amino acids. The relevant cellular receptors that mediate the biological effects of Nrg4, particularly on glucose and lipid metabolism and NAFLD, have not been established.

The foregoing observations provide evidence of the continuing need for compositions and formulations useful in treating diseases such as type 2 diabetes, cardiovascular disease, and non-alcoholic fatty liver disease (NAFLD).

SUMMARY

Nrg4 was identified as an adipocyte-derived factor that targets hepatocytes in the liver. The expression of Nrg4 was markedly decreased in adipose tissues in mouse models of obesity. Using Nrg4 knockout mice, it was determined that Nrg4 deficiency exacerbates diet-induced hyperglycemia, hyperlipidemia, and hepatic steatosis. In contrast, fat-specific transgenic expression of Nrg4 significantly improved these metabolic parameters following high-fat diet feeding. Together, these studies identified Nrg4 as a novel target for the development of therapeutic biologic for the treatments of type 2 diabetes, hyperlipidemia, and NAFLD.

In one aspect of the disclosure, there is provided a method of treating a metabolic disorder comprising administering to a patient in need thereof a therapeutically effective amount of Nrg4, an Nrg4 variant, or a biologically active fragment thereof.

In some embodiments, the metabolic disorder is selected from the group consisting of non-alcoholic fatty liver disease (NAFLD), steatohepatitis, type II diabetes, hyperglycemia, hyperlipidemia, dyslipidemia, obesity, hyperinsulinemia, insulin resistance, hypercholesterolemia, non-familial hypercholesterolemia, familial hypercholesterolemia, heterozygous familial hypercholesterolemia, homozygous familial hypercholesterolemia, mixed dyslipidemia, atherosclerosis, early onset coronary heart disease, dyslipidemia, hypertriglyceridemia, hyperfattyacidemia, and cirrhosis.

In some embodiments, the biologically active fragment comprises residues 5-46, 5-55, 5-62, 1-46, 1-55, 1-52, 1-53, 4-52, 4-53, or 1-62 of SEQ ID NO: 1.

In some embodiments, the Nrg4 variant is at least 70%, 75%, 80%, 85%, 90%, 95%, or 99% identical to SEQ ID NO: 1.

In some embodiments, the Nrg4, Nrg4 variant, or biologically active fragment thereof is encoded by a viral vector.

In some embodiments, the Nrg4, Nrg4 variant, or biologically active fragment thereof is chemically synthesized or purified from recombinant sources.

In another aspect of the disclosure, there is provided a method of treating a disease or condition characterized by a deficiency in neuregulin 4 (Nrg4) comprising administering to a patient in need thereof a therapeutically effective amount of Nrg4 (SEQ ID NO: 1), an Nrg4 variant, or a biologically active fragment thereof.

In some embodiments, the disease or condition is reduced expression of NRG4 in adipose tissue compared to expression of NRG4 in adipose tissue from a healthy patient. In some embodiments, the adipose tissue is brown adipose tissue or white adipose tissue.

In some embodiments, the disease or condition is aberrant communication between adipocytes and body tissues.

In some embodiments, the disease or condition is a metabolic disorder. In some embodiments, the metabolic disorder is selected from the group consisting of non-alcoholic fatty liver disease (NAFLD), steatohepatitis, type II diabetes, hyperglycemia, hyperlipidemia, dyslipidemia, obesity, hyperinsulinemia, insulin resistance, hypercholesterolemia, non-familial hypercholesterolemia, familial hypercholesterolemia, heterozygous familial hypercholesterolemia, homozygous familial hypercholesterolemia, mixed dyslipidemia, atherosclerosis, early onset coronary heart disease, dyslipidemia, hypertriglyceridemia, hyperfattyacidemia, and cirrhosis.

In some embodiments, the biologically active fragment comprises residues 5-46, 5-55, 5-62, 1-46, 1-55, 1-52, 1-53, 4-52, 4-53, or 1-62 of SEQ ID NO: 1.

In some embodiments, the Nrg4 variant is at least 70%, 75%, 80%, 85%, 90%, 95%, or 99% identical to SEQ ID NO: 1.

In some or any embodiments, the Nrg4, Nrg4 variant, or biologically active fragment thereof is encoded by a viral vector.

In some embodiments, the Nrg4, Nrg4 variant, or biologically active fragment thereof is chemically synthesized or purified from recombinant sources.

In another aspect of the disclosure, there is provided a method of treating a condition selected from the group consisting of non-alcoholic fatty liver disease (NAFLD), steatohepatitis, type II diabetes, hyperglycemia, hyperlipidemia, dyslipidemia, obesity, hyperinsulinemia, insulin resistance, hypercholesterolemia, non-familial hypercholesterolemia, familial hypercholesterolemia, heterozygous familial hypercholesterolemia, homozygous familial hypercholesterolemia, mixed dyslipidemia, atherosclerosis, early onset coronary heart disease, dyslipidemia, hypertriglyceridemia, hyperfattyacidemia, and cirrhosis comprising administering to a patient in need thereof a therapeutically effective amount of Nrg4, an Nrg4 variant, or a biologically active fragment thereof. In some embodiments, the biologically active fragment comprises residues 5-46, 5-55, 5-62, 1-46, 1-55, 1-52, 1-53, 4-52, 4-53, or 1-62 of SEQ ID NO: 1. In some embodiments, the Nrg4 variant is at least 70%, 75%, 80%, 85%, 90%, 95%, or 99% identical to SEQ ID NO: 1.

In yet another aspect of the disclosure, there is provided a method of reducing fat accumulation in the liver comprising administering to a patient in need thereof a therapeutically effective amount of Nrg4, an Nrg4 variant, or a biologically active fragment thereof. In some embodiments, the Nrg4, Nrg4 variant, or biologically active fragment thereof is co-administered with a therapeutically effective amount of a lipid-lowering agent. In some embodiments, the lipid-lowering agent is selected from the group consisting of atorvastatin, simvastatin, rosuvastatin, fluvastatin, ezetimibe, bezafibrate, ciprofibrate, clofibrate, niacin, gemfibrozil, and fenofibrate.

In yet another aspect of the disclosure, there is provided a method of reducing blood glucose levels comprising administering to a patient in need thereof a therapeutically effective amount of Nrg4, an Nrg4 variant, or a biologically active fragment thereof. In some embodiments, the Nrg4, Nrg4 variant, or biologically active fragment thereof is co-administered with a therapeutically effective amount of insulin, GLP-1, metformin, or a DPP4 inhibitor.

In yet another aspect of the disclosure, there is provided a pharmaceutical composition comprising Nrg4, an Nrg4 variant, or a biologically active fragment thereof and a pharmaceutically acceptable carrier. In some embodiments, the biologically active fragment comprises residues 5-46, 5-55, 5-62, 1-46, 1-55, 1-52, 1-53, 4-52, 4-53, or 1-62 of SEQ ID NO: 1. In some embodiments, the Nrg4 variant is at least 70%, 75%, 80%, 85%, 90%, 95%, or 99% identical to SEQ ID NO: 1.

In still another aspect of the disclosure, there is provided a method of diagnosing a metabolic disorder in a test individual comprising the step of determining a Nrg4 level in a sample from the test individual, wherein a Nrg4 level that is reduced in the test individual compared to a Nrg4 level in a normal individual is suggestive of the condition and wherein the normal individual is known not to suffer from the metabolic disorder.

In another aspect of the disclosure, there is provided a method for diagnosing a metabolic disorder in an individual comprising the step of detecting Nrg4 levels in a sample from the individual, wherein a Nrg4 level that is reduced compared to a prior Nrg4 level in the same individual is suggestive of the metabolic disorder.

In another aspect of the disclosure, there is provided a method for determining susceptibility to a metabolic disorder in a test individual comprising the step of determining a Nrg4 level in a sample from the test individual, wherein a reduced Nrg4 level in the test individual compared to Nrg4 level in a sample from a normal individual indicates susceptibility to the condition, and wherein the normal individual is known not to suffer from the metabolic disorder.

In another aspect of the disclosure, there is provided a method for determining susceptibility to a metabolic disorder in an individual comprising the step of detecting a Nrg4 level in a sample from the individual, wherein a Nrg4 level that is reduced in the individual compared to a prior Nrg4 level in the same individual is suggestive of susceptibility to the metabolic disorder.

In another aspect of the disclosure, there is provided a method for determining the progression of a metabolic disorder in an individual comprising the step of determining Nrg4 levels in samples from the individual over time, wherein a decrease in Nrg4 level over time is suggestive of progression of the metabolic disorder.

In another aspect of the disclosure, there is provided a method for monitoring the effectiveness of treatment of a metabolic disorder in an individual comprising the step of determining Nrg4 levels in samples from the individual over time, wherein an increase in Nrg4 level over time is suggestive of effective treatment.

In some embodiments of the methods of paragraphs [0018]-[0023], the metabolic disorder is selected from the group consisting of non-alcoholic fatty liver disease (NAFLD), steatohepatitis, type II diabetes, hyperglycemia, hyperlipidemia, dyslipidemia, obesity, hyperinsulinemia, insulin resistance, hypercholesterolemia, non-familial hypercholesterolemia, familial hypercholesterolemia, heterozygous familial hypercholesterolemia, homozygous familial hypercholesterolemia, mixed dyslipidemia, atherosclerosis, early onset coronary heart disease, dyslipidemia, hypertriglyceridemia, hyperfattyacidemia, and cirrhosis.

In some embodiments of the above methods, a Nrg4 level is a measure of serum protein concentration of the Nrg4.

In some embodiments, a Nrg4 level is a measure of NRG4 mRNA levels.

In some embodiments, a Nrg4 level is a measure of Nrg4 activity.

In some embodiments, Nrg4 activity is specific binding activity.

In another aspect, the disclosure includes uses of Nrg4 for the preparation of medicaments. In another aspect, the disclosure includes use of Nrg4 and compositions comprising Nrg4 for the treatment of NAFLD, steatohepatitis, type II diabetes, hyperglycemia, hyperlipidemia, dyslipidemia, obesity, hyperinsulinemia, insulin resistance, hypercholesterolemia, non-familial hypercholesterolemia, familial hypercholesterolemia, heterozygous familial hypercholesterolemia, homozygous familial hypercholesterolemia, mixed dyslipidemia, atherosclerosis, early onset coronary heart disease, dyslipidemia, hypertriglyceridemia, hyperfattyacidemia, and cirrhosis. Other related aspects are also provided in the disclosure.

Other features and advantages of the present disclosure will become apparent from the following detailed description. It should be understood, however, that the detailed description and the specific examples, while indicating preferred embodiments of the disclosure, are given by way of illustration only, because various changes and modifications within the spirit and scope of the disclosure will become apparent to those skilled in the art from this detailed description.

BRIEF DESCRIPTIONS OF THE DRAWINGS

FIG. 1: Alignment of human and mouse Nrg4 protein sequences. The EGF-like domain is characterized by the presence of three conserved disulfide bonds (bars linking Cys residues). Putative N-linked glycosylation site ($N^{39}YT$), proteolytic cleavage sites (arrows), and predicted transmembrane domain (TM) are indicated. Note that the EGF-like domain (amino acid 1 to approximately amino acid 52) of human and mouse Nrg4 is highly conserved.

Figure 2:
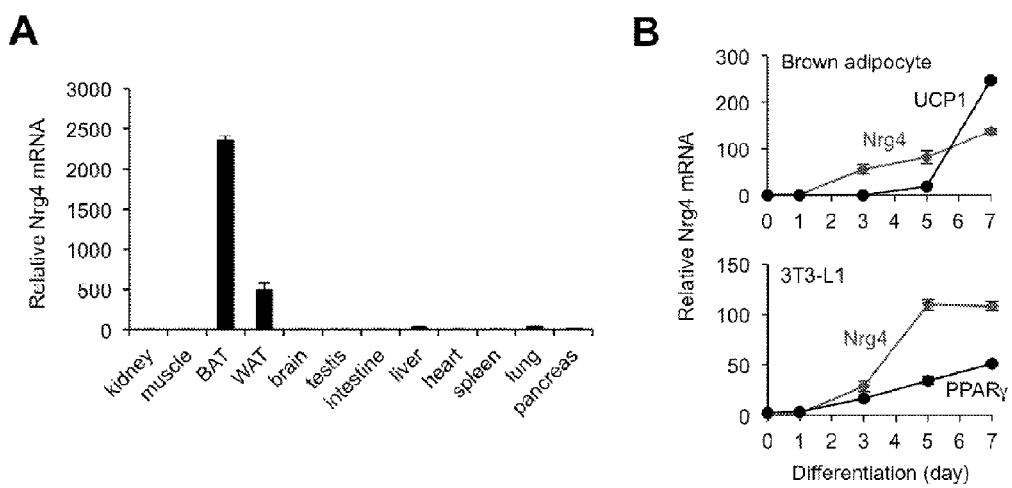

FIG. 2: Expression of Nrg4 in adipose tissues and in cultured adipocytes. (A) Taqman quantitative PCR analysis of Nrg4 mRNA in different tissues. Nrg4 is abundantly expressed in brown adipose tissue (BAT) and white adipose tissue (WAT). Pooled RNA samples from three C57BL/6J male mice were analyzed. (B) Nrg4 mRNA expression is induced during differentiation of brown (top) and white (3T3-L1, bottom) adipocytes. UCP1 and PPARγ were included as differentiation markers. Shown are mean±stdev from triplicate wells of one representative study.

Figure 3:
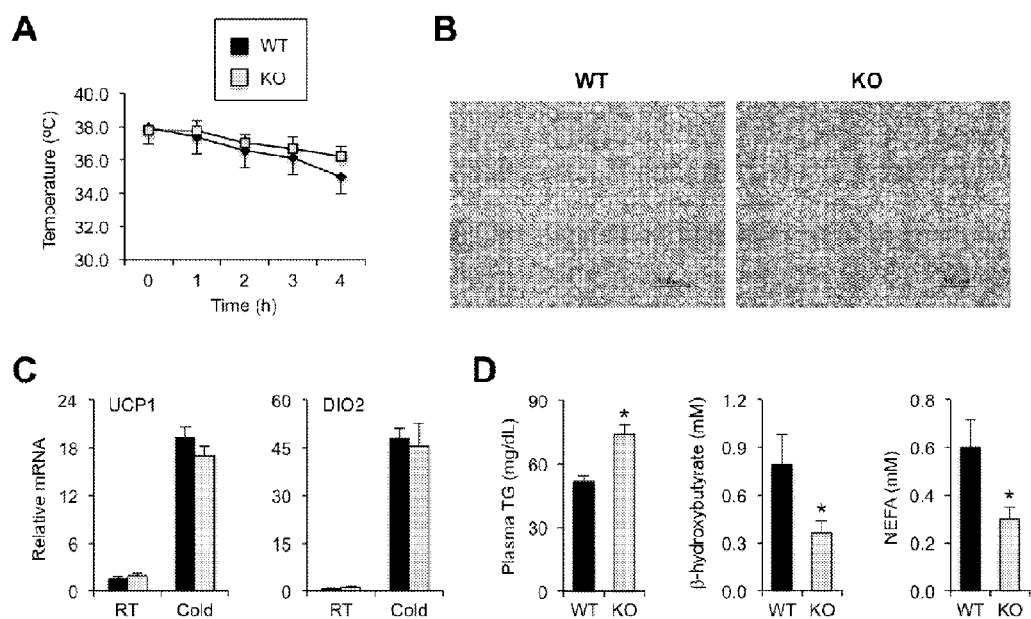

FIG. 3: Nrg4 deficient mice are cold-tolerant and have normal cold-induced thermogenesis. (A) Rectal temperature of wild type and Nrg4 KO mice following cold exposure. Mice were transferred from ambient temperature to 4° C. for a total of 4 hours with free access to food and water. (B) Histology (H&E) of interscapular brown adipose tissue (scale bar=100 µm). (C) qPCR analyses of BAT gene expression in mice exposed to ambient room temperature (RT, WT=5, KO=6) or cold temperature (Cold, WT=5, KO=7). (D) Plasma triglycerides (TG), ketone (β-hydroxybutyrate), and non-esterified fatty acid (NEFA) concentrations in WT and Nrg4 KO mice following cold exposure.

Figure 4:
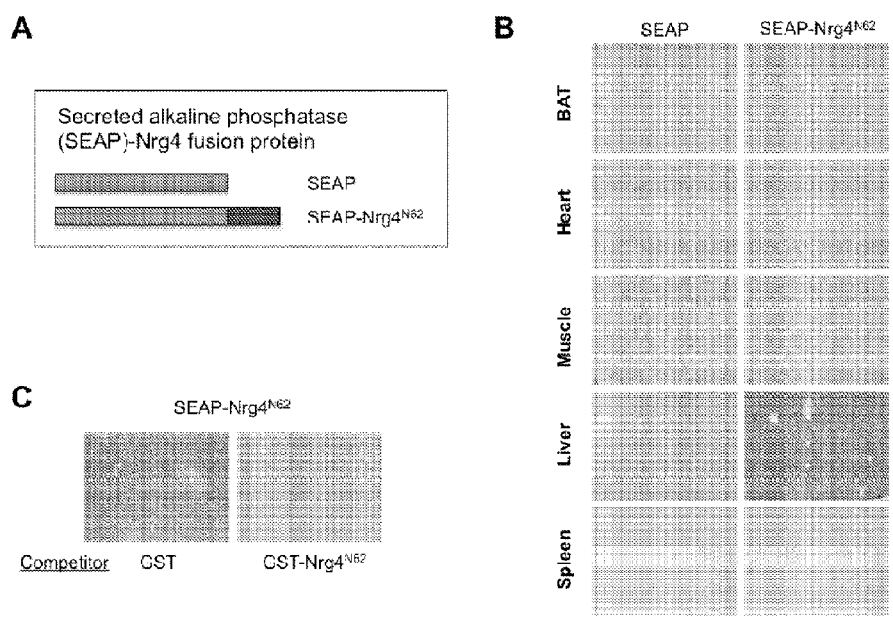

FIG. 4: The EGF-like domain of Nrg4 binds to hepatocytes. (A) Schematic diagram of secreted alkaline phosphatase (SEAP) control or SEAP-Nrg4 fusion protein (amino acids 1-62). (B) SEAP-Nrg4$^{N62}$ specifically binds to hepatocytes, but not cells in BAT, heart, muscle, and spleen. (C) Excess GST-Nrg4$^{N62}$ fusion protein competes for Nrg4 binding sites present on hepatocytes. Liver sections were incubated with SEAP-Nrg4$^{N62}$ in the presence of 3.0 µg/mL GST or GST-Nrg4 recombinant proteins.

Figure 5:
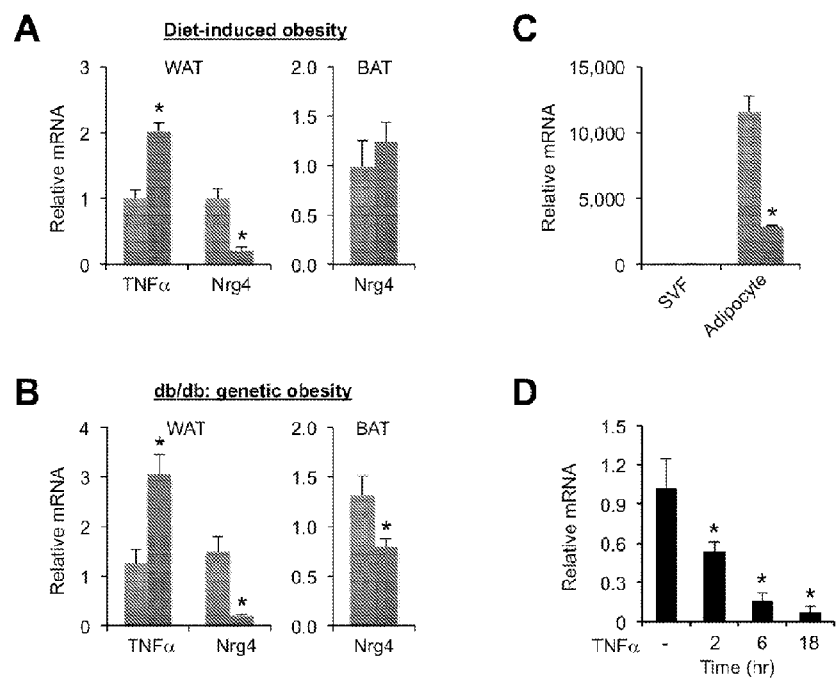

FIG. 5: Regulation of adipose Nrg4 expression by obesity. (A) qPCR analysis of Nrg4 mRNA levels in WAT and BAT from lean or diet-induced obese mice. Wild type C57BL/6J male mice were maintained on standard chow (n=5) or high-fat diet (n=6) for 3 months. Total RNA was isolated from adipose tissues for qPCR analysis. (B) qPCR analysis of Nrg4 mRNA levels in adipose tissues from WT (n=5) or leptin receptor deficient db/db (n=6) mice. Data in A-B are mean±SEM. *p<0.05. (C) qPCR analysis of Nrg4 mRNA levels in stromal vascular fraction (SVF) and adipocyte fraction isolated from epididymal WAT from mice fed standard chow (n=3) or high-fat diet (n=3). *p<0.01 chow vs. HFD. (D) Nrg4 expression in mature 3T3-L1 adipocytes treated with vehicle (−) or TNFα (10 ng/mL) for indicated time. Shown are mean±stdev from triplicate wells of one representative study. *p<0.01 TNFα vs. vehicle.

Figure 6:
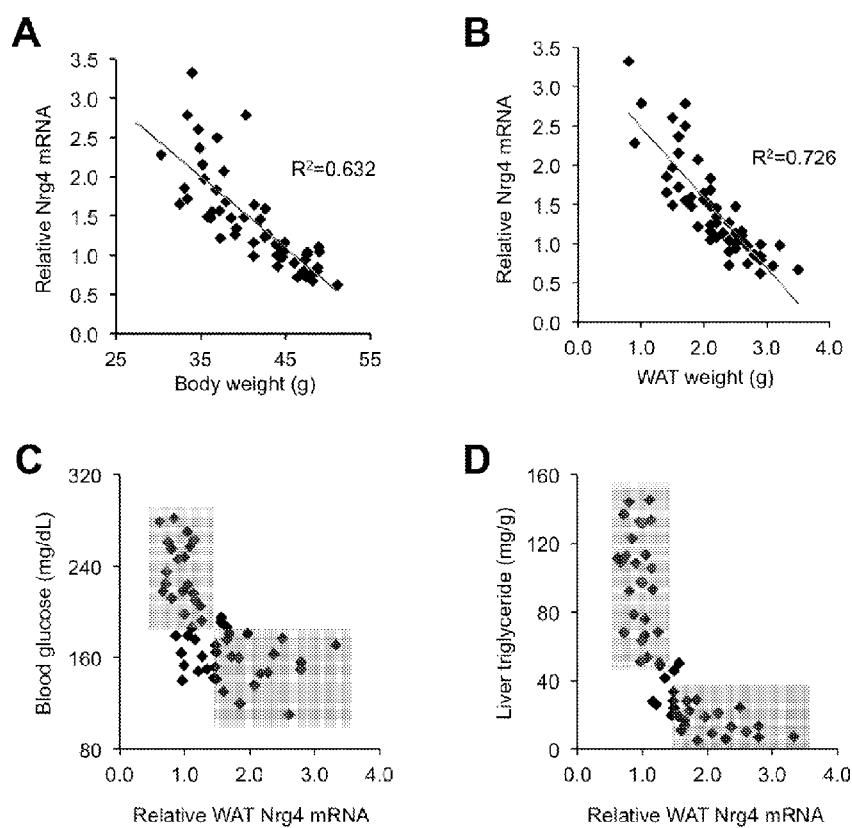

FIG. 6: Correlation between Nrg4 expression levels and metabolic parameters. A group of 54 wild type C57BL/6J male mice were fed with high-fat diet for two months. Relative Nrg4 mRNA expression in epididymal WAT and metabolic parameters were measured. (A-B) Nrg4 mRNA expression inversely correlates with body weight (A) and epididymal white fat weight (B). (C) High Nrg4 (lower box) and low Nrg4 (upper box) expression levels are associated with low and high blood glucose levels, respectively. (D) High Nrg4 (lower box) and low Nrg4 (upper box) expression levels are associated with low and high hepatic fat content, respectively.

Figure 7:
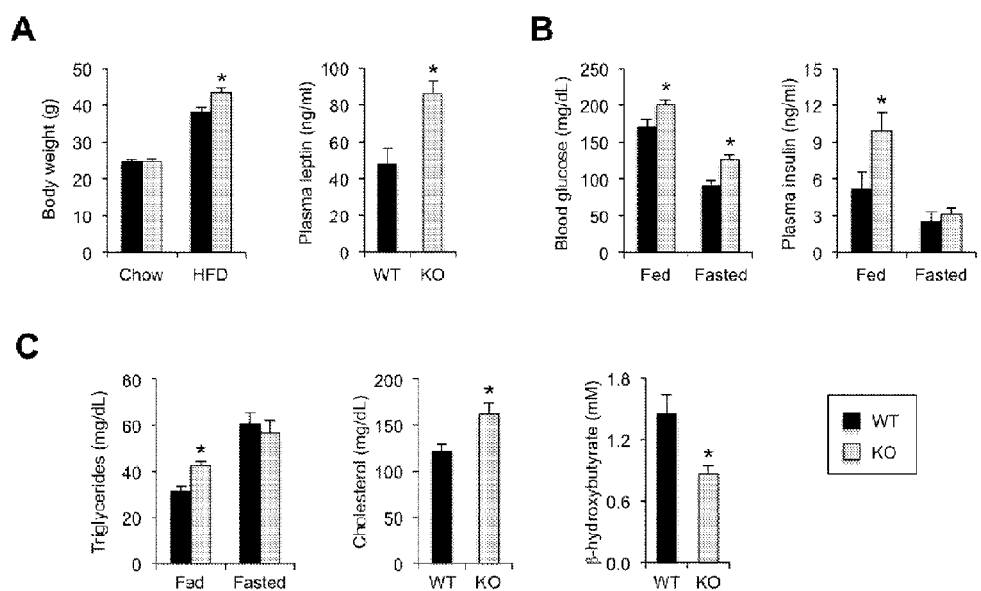

FIG. 7: Nrg4 deficiency exacerbates diet-induced insulin resistance and hyperlipidemia. (A) Body weight of wild type (filled, n=8) and Nrg4 KO (grey, n=9) mice fed chow or a high-fat diet (HFD). Plasma leptin levels were measured 8 weeks after HFD feeding. (B) Plasma glucose and insulin levels measured under fed and fasted conditions. (C) Plasma concentrations of triglycerides, total cholesterol, and β-hydroxybutyrate. Data represent mean±SEM. *p<0.05.

Figure 8:
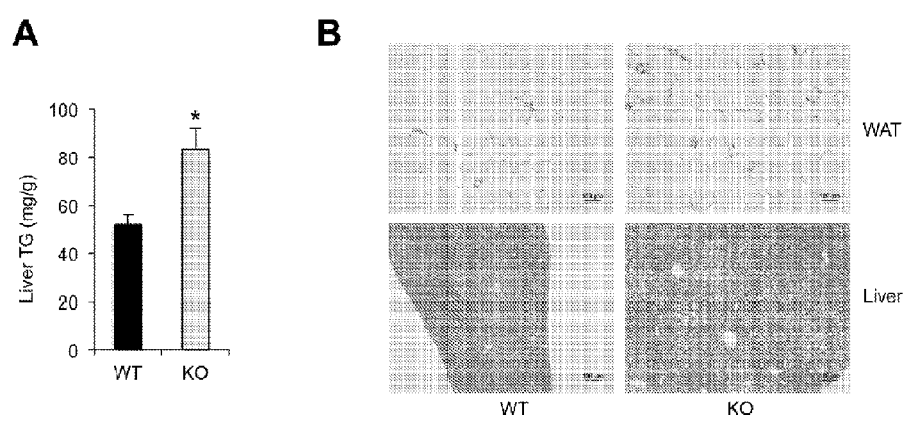

FIG. 8: Nrg4 deficiency exacerbates diet-induced hepatic steatosis. (A) Liver triglyceride content in wild type (filled, n=9) and Nrg4 KO (grey, n=8) mice fed HFD for 7 weeks. Data represent mean±SEM. *p<0.05. (B) H&E staining of epididymal WAT and liver sections from WT and Nrg4 KO mice 7 weeks after HFD. Scale bar=100 µM.

Figure 9:
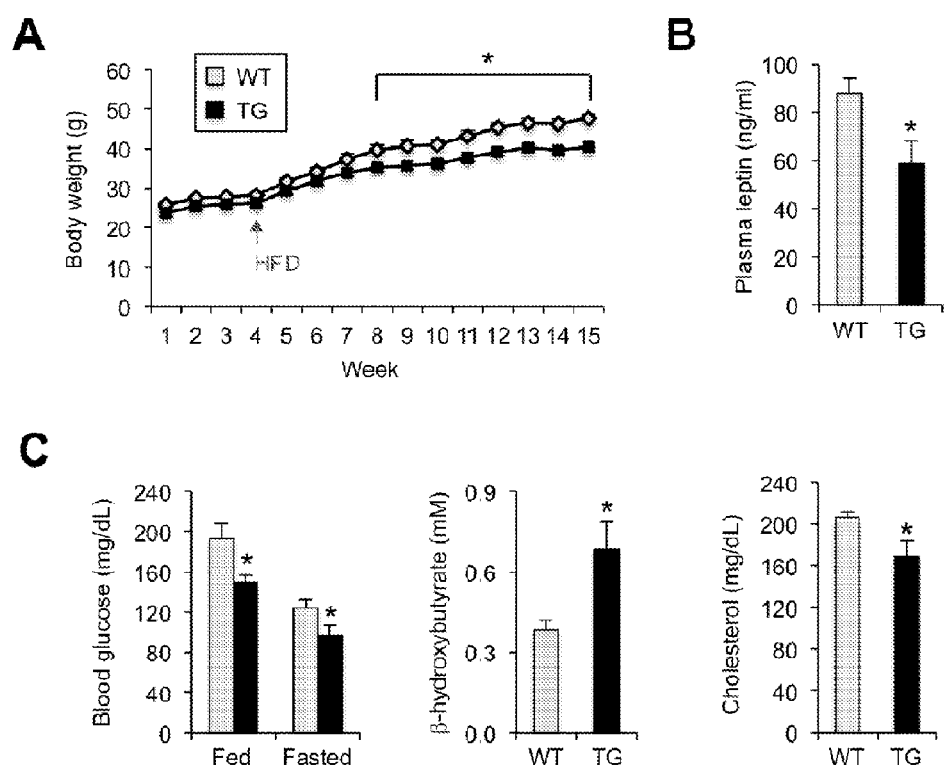

FIG. 9: Transgenic expression of Nrg4 in adipose tissues protects mice from diet-induced metabolic disorders. (A) Fat-specific Nrg4 transgenic mice (TG) are protected from diet-induced obesity. (B) Plasma leptin concentrations in WT (n=10) and TG (n=9) mice following 8 weeks of high-fat feeding. (C) Plasma glucose (fed and fasted), total cholesterol (fed), and β-hydroxybutyrate (fasted) concentrations in WT and TG mice. Data in A-C represent mean±SEM. *p<0.05.

Figure 10:
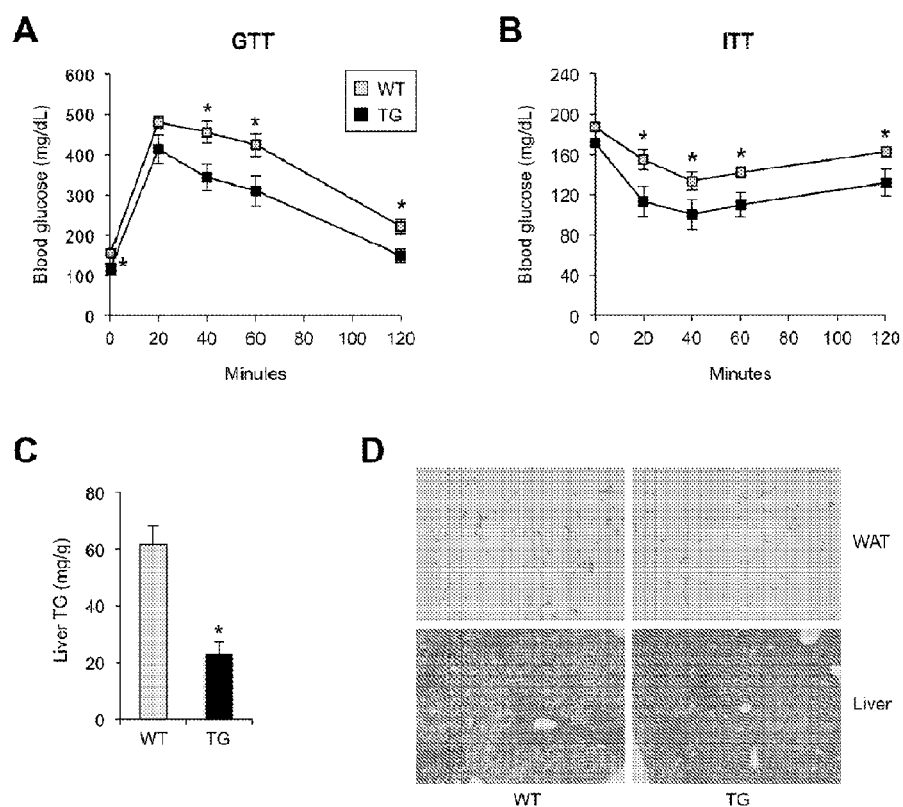

FIG. 10: Nrg4 transgenic mice are more glucose tolerant, insulin sensitive, and protected from diet-induced fatty liver. (A) Glucose tolerance test in WT and TG mice following 10 weeks of high-fat feeding. (B) Insulin tolerance test in WT and TG mice following 12 weeks of high-fat feeding. Data in A-B represent mean±SEM (n=8-10). *p<0.05. (C) Liver triglyceride content in WT (grey, n=9) and TG (filled, n=9) mice fed HFD for 11 weeks. Data represent mean±SEM. *p<0.05. (D) H&E staining of epididymal WAT and liver sections.

Figure 11:
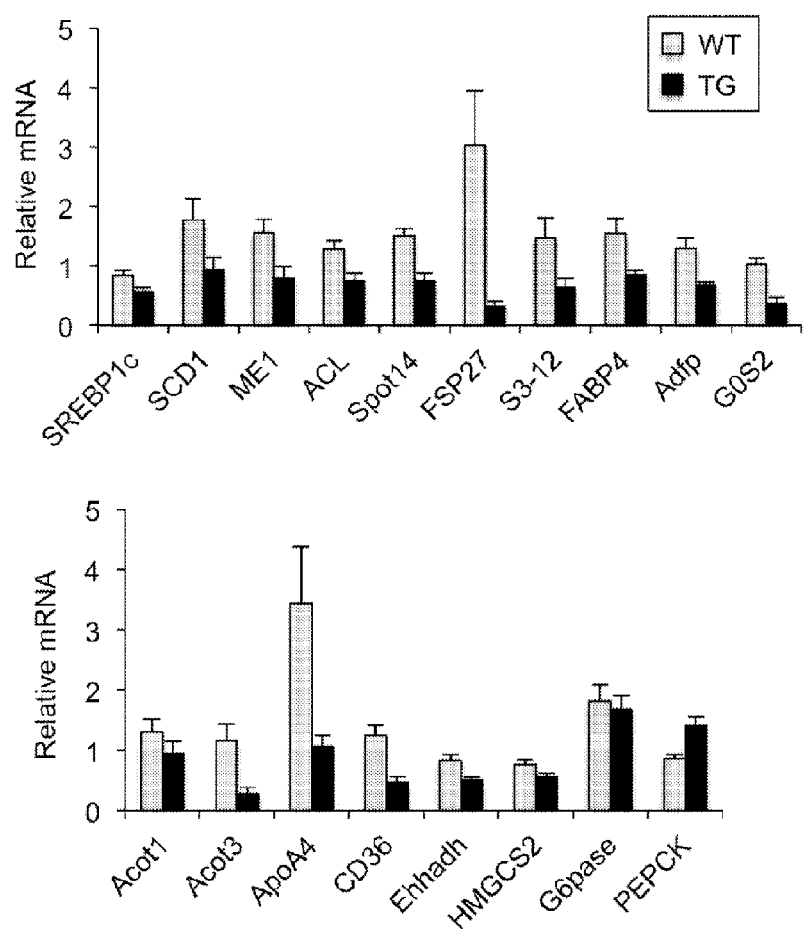

FIG. 11: qPCR analyses of liver gene expression in WT and TG mice following 11 weeks of HFD feeding. Data represent mean±SEM. *p<0.05.

Figure 12:
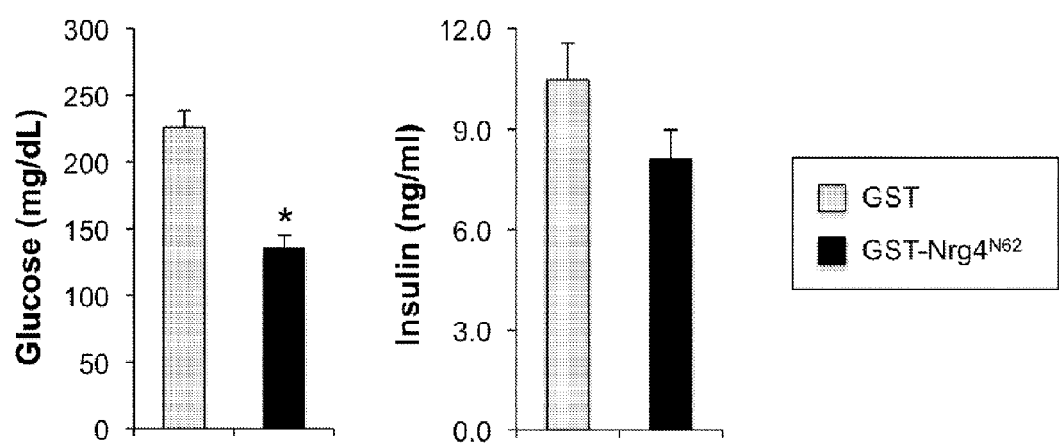

FIG. 12: Recombinant Nrg4 lowers blood glucose in diet-induced obese mice. HFD-fed obese mice were injected intraperitoneally with GST or GST-Nrg4$^{N62}$ twice (4 µg per gram of body weight) for a total of 6 hrs. Note that Nrg4 lowers blood glucose levels not through promoting insulin secretion.

Figure 13:
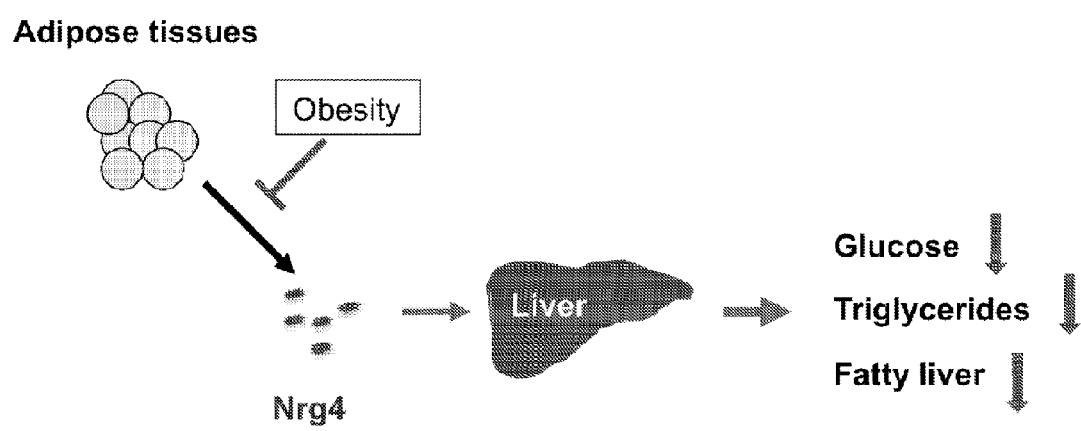

FIG. 13: Model depicting Nrg4 as a potential therapeutic biologic for treating type 2 diabetes and non-alcoholic fatty liver disease. Nrg4 is an adipocyte-derived hormone that acts on the liver to lower blood glucose and lipids and reduce hepatic fat content.

Figure 14:
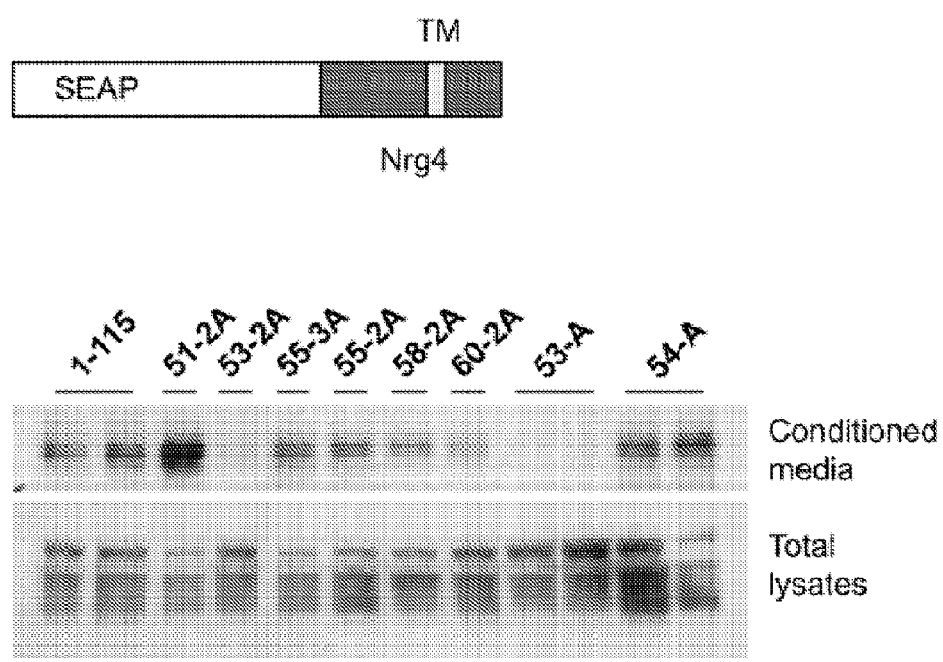

FIG. 14: Mapping of amino acids important for the release of the extracellular fragment of Nrg4. SEAP-Nrg4 fusion vectors were constructed between SEAP cDNA and full-length Nrg4, a.a.1-115 and transiently transfected into HEK293 cells. The positions of Alanine mutants are indicated above the Immunoblots. Conditioned media and total cell lysates were harvested and analyzed by immunoblotting with anti-SEAP antibody. Note that mutations of amino acids 53-54 or 53 markedly reduced the secretion of fusion proteins into media.

Figure 15:
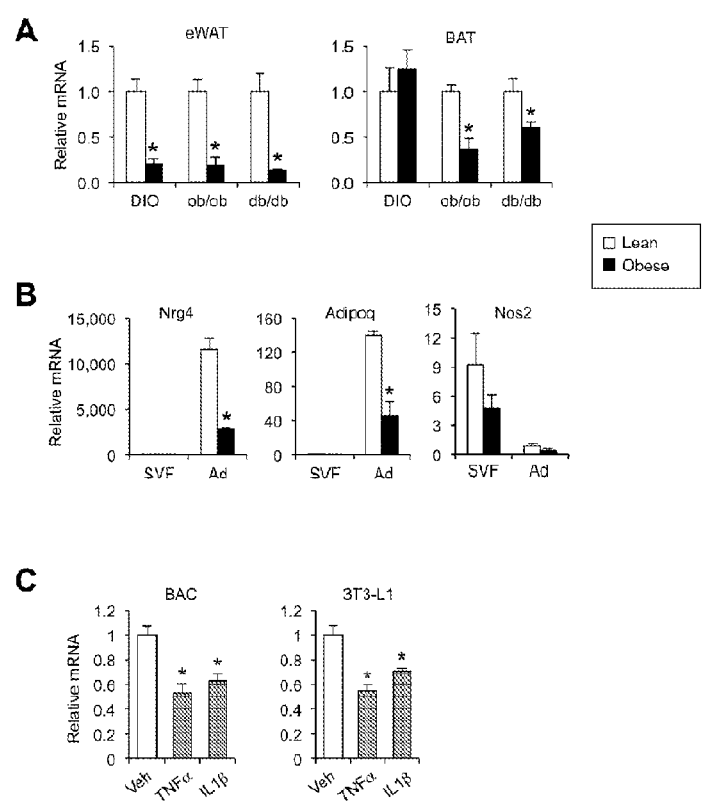

FIG. 15: Reduced expression of Nrg4 in brown and white adipose tissues in mouse models of obesity. (A) qPCR analysis of Nrg4 mRNA expression in epididymal white fat (eWAT) and BAT from lean (open bars) or obese (black bars) mice. For DIO, WT male mice were fed standard chow (n=5) or HFD (n=6) for three months. For genetic obesity, a group of WT (n=3) and ob/ob (n=4) and a separate group of WT (n=5) and db/db (n=6) mice were analyzed. (B) qPCR analysis of Nrg4 mRNA expression in stromal vascular fraction (SVF) and adipocyte fraction (Ad) isolated from eWAT from lean (n=3) or DIO (n=3) mice. Data in a-b represent mean±s.e.m. *p<0.05. (C) qPCR analysis of Nrg4 mRNA expression in differentiated brown or 3T3-L1 adipocytes following treatments with vehicle (Veh), TNFα (10 ng/ml), or IL1β (40 ng/ml) for 6 hrs. Data represent mean±s.d. from one representative study performed in triplicates. *p<0.05 vs. Veh.

Figure 16:
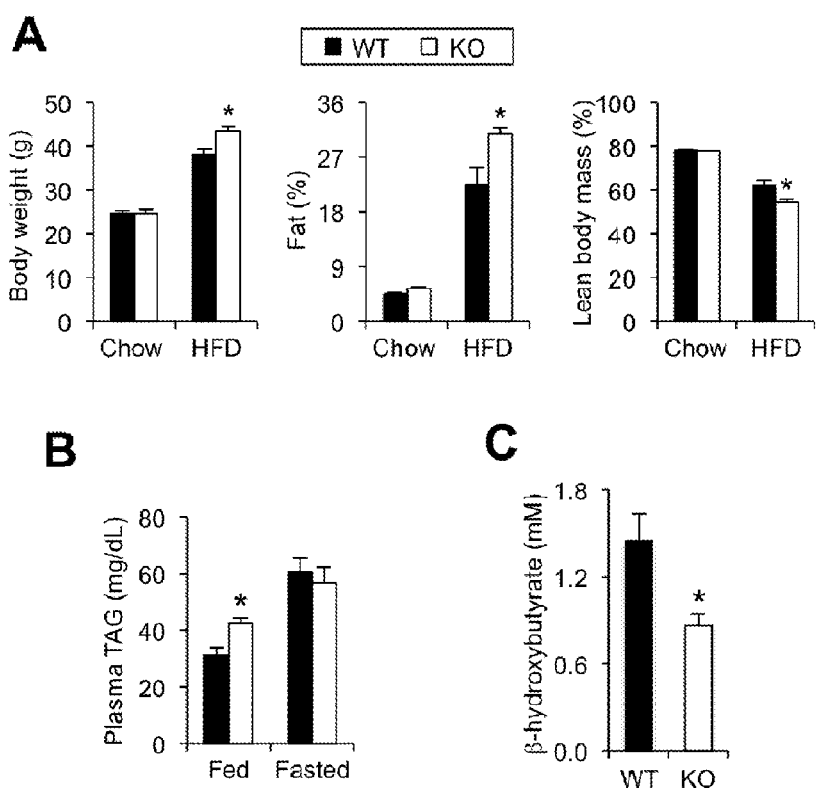

FIG. 16: Nrg4 deficiency exacerbates diet-induced obesity and elevates plasma triglyceride levels. (A) Body weight, adiposity, and percent lean body mass in wild type (filled, n=8) and Nrg4 KO (grey, n=9) mice fed chow or HFD. (B) Plasma TAG levels in WT and Nrg4 KO mice under fed and fasted conditions. (C) Plasma concentrations of β-hydroxybutyrate. Data represent mean±SEM. *p<0.05.

Figure 17:
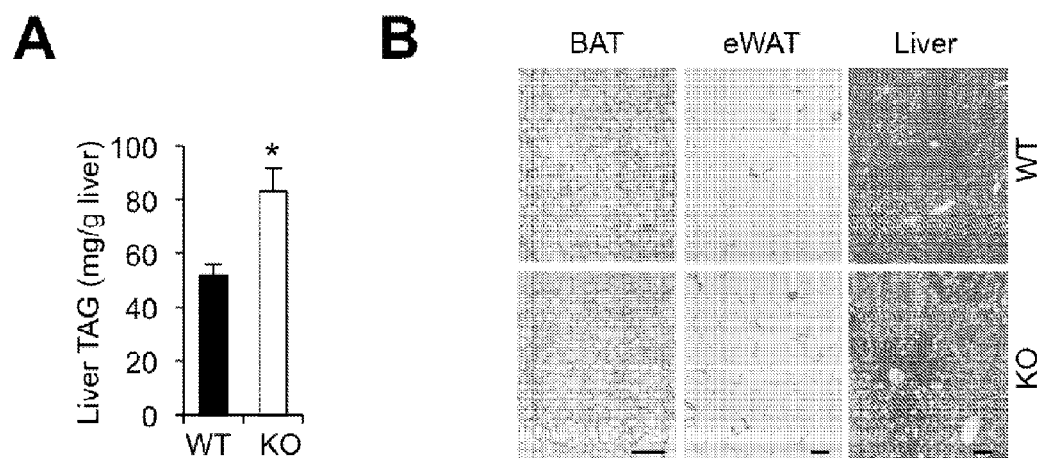

FIG. 17: Nrg4 deficiency exacerbates diet-induced hepatic steatosis. (A) Liver triglyceride content in wild type (filled, n=9) and Nrg4 KO (grey, n=8) mice fed HFD for 7 weeks. Data represent mean±SEM. *p<0.05. (B) H&E staining of BAT, epididymal WAT and liver sections from WT and Nrg4 KO mice 7 weeks after HFD. Scale bar=100 μM.

Figure 18:
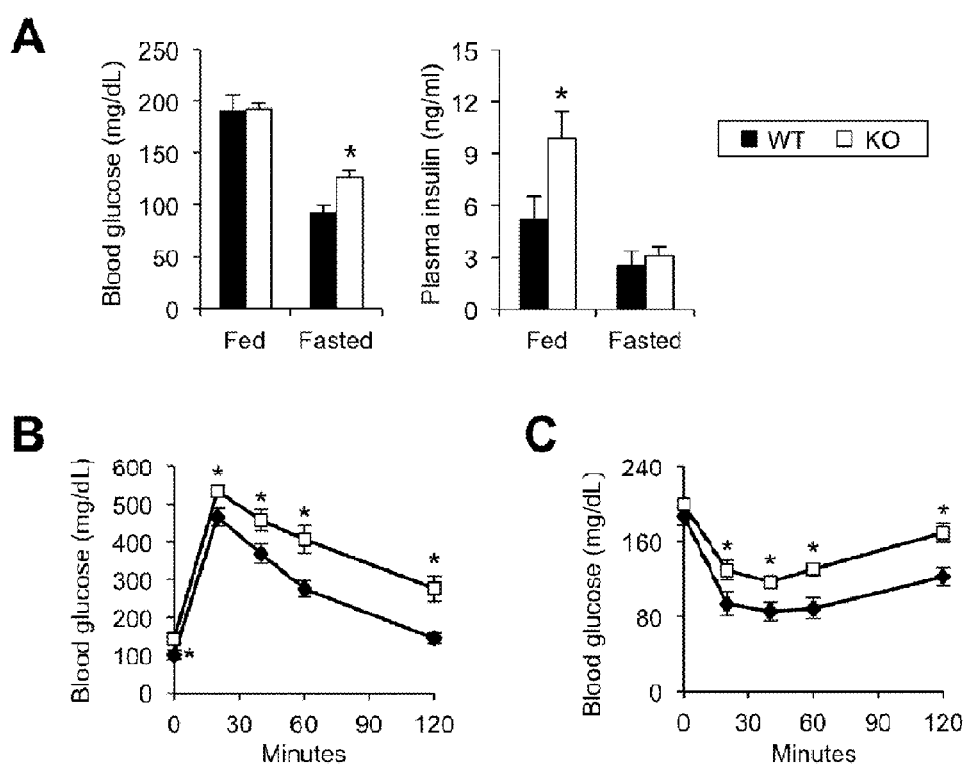

FIG. 18: Nrg4 null mice developed more severe high-fat diet-induced glucose intolerance and insulin resistance. (A) Fed and fasted blood glucose and fasted plasma insulin levels in HFD-fed WT and KO mice. (B) Glucose tolerance test in WT (n=7, filled diamond, black line) and Nrg4 KO (n=7, open square, red line) mice after 13 weeks on HFD. (C) Insulin tolerance test in WT (n=7) and Nrg4 KO (n=9) mice after 15 weeks on HFD. Data represent mean±s.e.m. *p<0.05, KO vs. WT.

Figure 19:
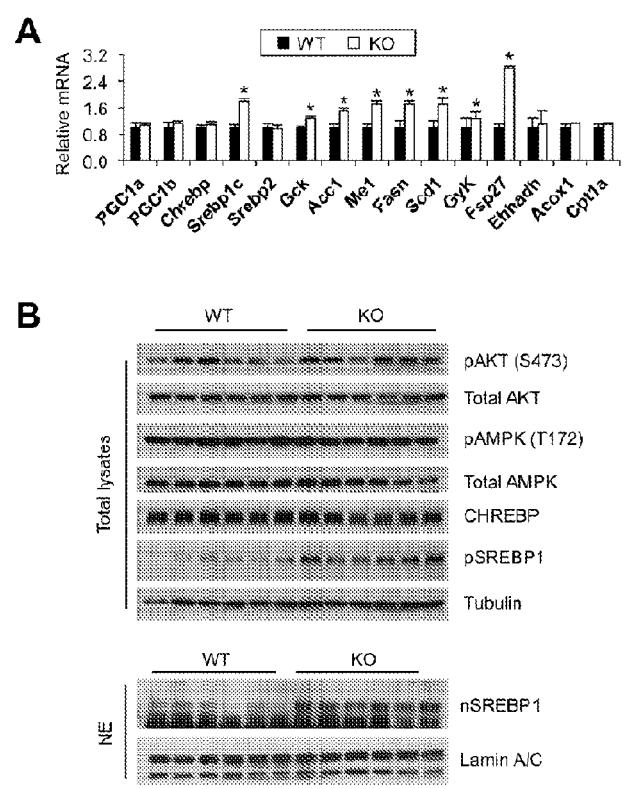

FIG. 19: Nrg4 deficiency promotes aberrant activation of hepatic lipogenic gene program. (A) qPCR analysis of hepatic gene expression in ad lib WT and Nrg4 KO mice. Data represent mean±s.e.m. *p<0.05, KO vs. WT. (B) Liver tissues were dissected from HFD-fed WT and Nrg4 KO mice and processed for qPCR and immunoblotting analyses. Immunoblots of total liver lysates using indicated antibodies (top); pSREBP1 denotes precursor SREBP1 protein. Immunoblots of nuclear SREBP1 (nSREBP1) using liver nuclear extracts (bottom). Lamin A/C immunoblot was included as loading control.

Figure 20:
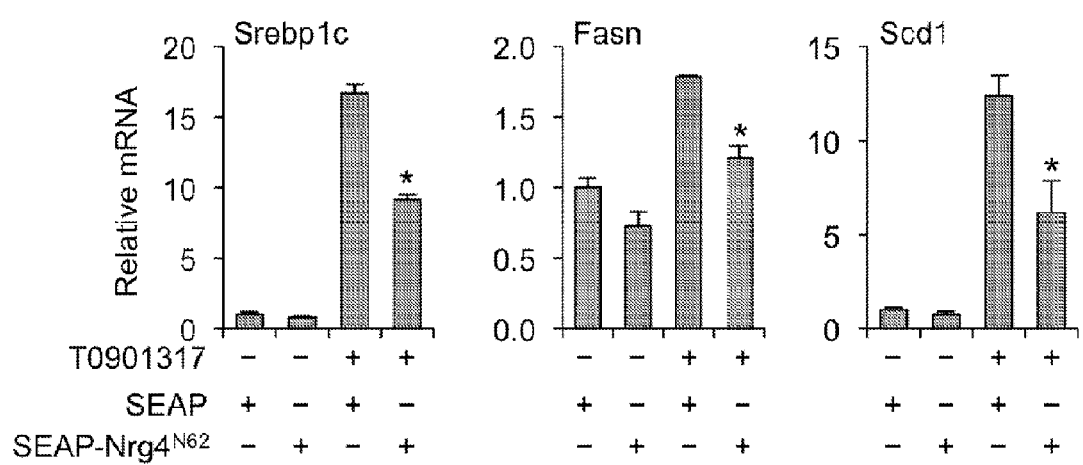

FIG. 20: Nrg4 attenuates the induction of lipogenic gene expression by LXR activation in primary hepatocytes. qPCR analysis of gene expression in primary hepatocytes treated with vehicle or T0901317 in the presence of conditioned media containing SEAP or SEAP-Nrg4N62. Data represent mean±s.d. *p<0.05.

Figure 21:
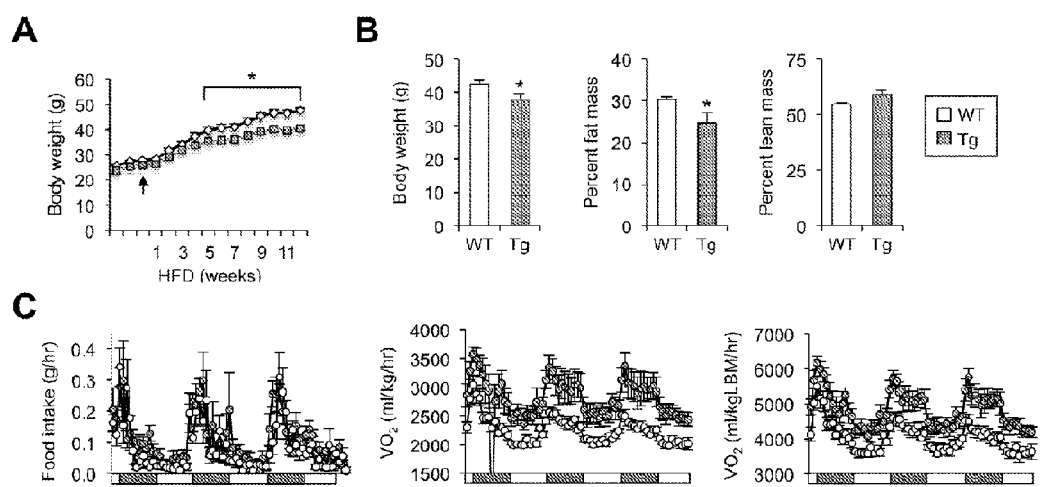

FIG. 21: Transgenic expression of Nrg4 in adipose tissues protects mice from diet-induced obesity. (A) Growth curve of WT (solid bars, n=10) and aP2-Nrg4 transgenic (Tg, open bars, n=9) mice before and after 12 weeks of HFD feeding. (B) Body composition. (C) Food intake and VO2 in WT and aP2-Nrg4 Tg mice following 6 weeks of HFD feeding. VO2 values were normalized to body weight (middle panel) and lean body mass (right panel).

Figure 22:
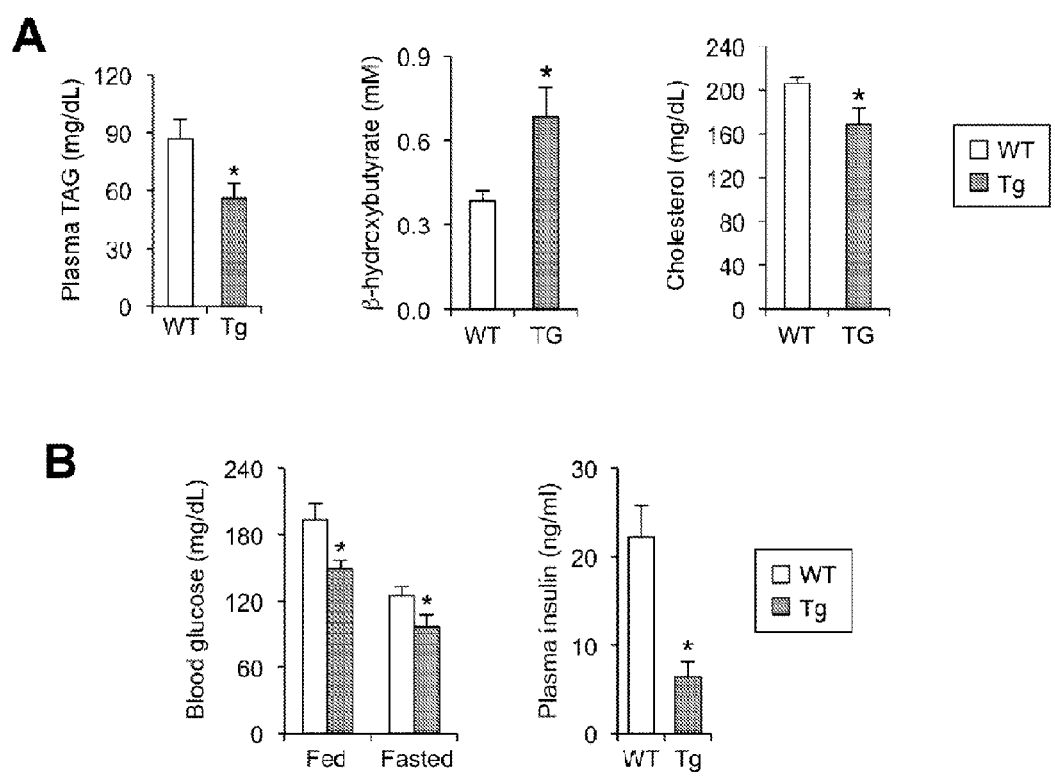

FIG. 22: Nrg4 transgenic mice are protected from HFD-induced metabolic disorders. (A) Plasma metabolite concentrations in WT (open bars, n=9) and Tg (solid bars, n=8) mice following 10 weeks of high-fat feeding. (B) Fed and fasted blood glucose and fasted plasma insulin levels in HFD-fed WT (open bars, n=9) and Tg (solid bars, n=8) mice. Data represent mean±s.e.m. *p<0.05, WT vs. Tg.

Figure 23:
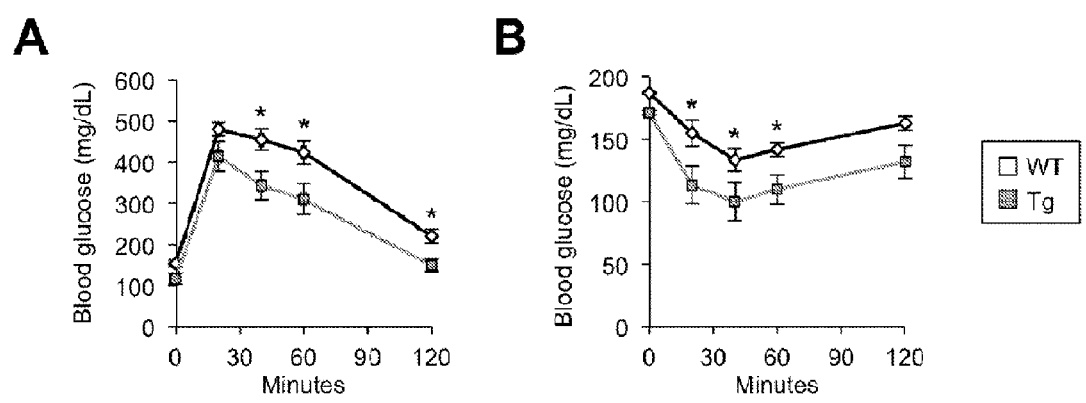

FIG. 23: Nrg4 transgenic mice are protected from HFD-induced glucose intolerance and insulin resistance. (A) Glucose tolerance test in HFD-fed WT (open, n=9) and Tg (solid, n=8) mice. (B) Insulin tolerance test in HFD-fed WT (open, n=9) and Tg (solid, n=8) mice. Data represent mean±s.e.m. *p<0.05, WT vs. Tg.

Figure 24:
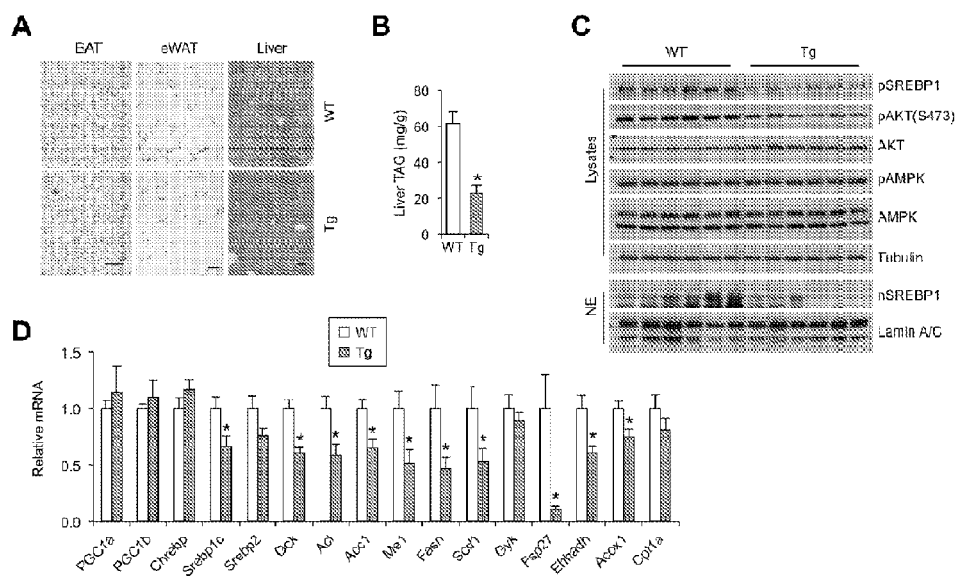

FIG. 24: Nrg4 transgenic mice are protected from HFD-induced fatty liver through attenuating hepatic lipogenesis. (A) H&E staining of adipose tissues and liver sections in HFD-fed mice. Scale bar=100 μm. (B) Liver TAG content. (C) Immunoblots using total liver lysates (top) and liver nuclear extracts (bottom). Note that the levels of precursor and nuclear SREBP1 were reduced in the liver from Tg mice. (D) qPCR analysis of hepatic gene expression in ad lib WT (open) and Tg (solid) mice. Data represent mean±s.e.m. *p<0.05, WT vs. Tg.

Figure 25:
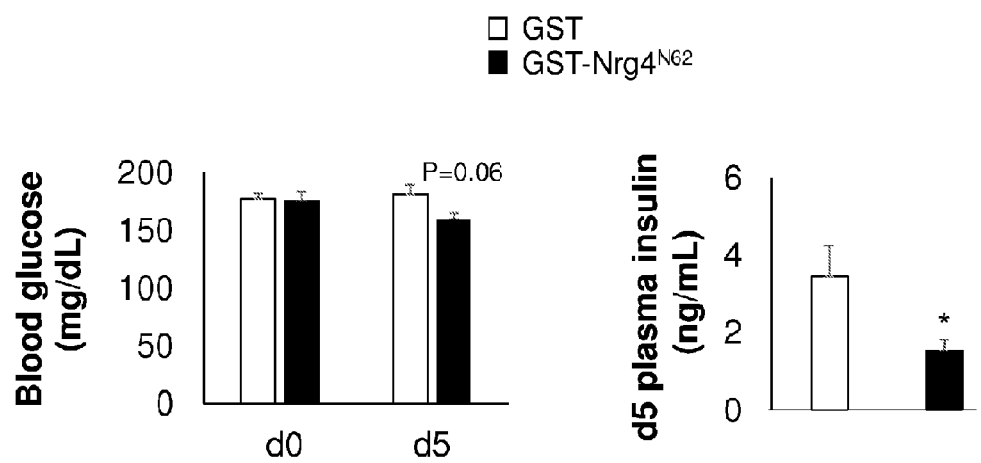

FIG. 25: Recombinant Nrg4 lowers blood glucose and insulin in diet-induced obese mice. HFD-fed obese mice were injected intraperitoneally with GST or GST-Nrg4$^{N62}$ twice (4 μg per gram of body weight) per day for a total of 5 days. Note that Nrg4 lowers blood glucose levels not through promoting insulin secretion.

DETAILED DESCRIPTION

Definitions

As used herein, the term "Nrg4" (SEQ ID NO: 1) refers to the protein encoded by the human NRG4 gene. Nrg4 was discovered based on its sequence homology to other NRG members and is predicted to encode a precursor protein of 115 amino acids. Nrg4 is highly conserved between mouse and human, with over 90% amino acid sequence identity in the EGF-like domain (approximately AA 1-52, FIG. 1). Thus, in some embodiments, the term "Nrg4" refers to SEQ ID NO: 2, i.e., the protein encoded by the mouse NRG4 gene.

As used herein, the term "treating" or "treatment" refers to administering a therapeutically effective amount of Nrg4, an Nrg4 variant, or a biologically active fragment thereof to a patient in need thereof as described herein to effect an alteration or improvement of the disease or condition. Treatment in certain aspects, requires administration of a single dose or multiple doses at regular intervals to alter the course of the condition.

As used herein, "administering" means providing a pharmaceutical agent to an animal, including a human patient, and includes, but is not limited to administering by a medical professional and self-administering.

As used herein, the term "co-administration" refers to administration of two or more pharmaceutical agents to an animal, including a human patient. In certain aspects, the pharmaceutical agents are in a single pharmaceutical composition or in separate pharmaceutical compositions. Co-administration includes administering each pharmaceutical agent through the same or different routes of administration. Co-administration also encompasses administration in parallel or sequentially.

As used herein, the term "therapeutically effective amount" refers to an amount of a pharmaceutical agent that provides a therapeutic benefit to an animal, including a human patient.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (Remington's, 1990).

As used herein, the term "metabolic disorder" refers to a condition characterized by an alteration or disturbance in metabolic function. "Metabolic" and "metabolism" are terms well know in the art and generally include the whole range of biochemical processes that occur within a living organism.

Nrg4 variants of the invention may comprise conservative substitutions of native amino acids at particular residues. Amino acid residues which share common side-chain properties and are appropriate for generating conservative substitutions are grouped as follows.
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Nrg4

Neuregulin 4 (Nrg4), a member of the neuregulin family of signaling ligands, was discovered herein as a novel fat-derived hormone that regulates plasma glucose and lipid levels and the development NAFLD. Nrg4 expression is highly enriched in adipose tissues and is induced during differentiation of brown and white adipocytes. Using a binding assay, it was found that Nrg4 binds exclusively to hepatocytes through a putative receptor (or receptors) in a saturable manner. The levels of Nrg4 expression in adipocytes are significantly reduced in diet-induced and genetic models of obesity in mice, suggesting that Nrg4 insufficiency may contribute to the development of obesity-associated metabolic disorders. In support of this, Nrg4 null mice developed more severe hyperglycemia, hyperlipidemia, and hepatic steatosis following high-fat diet feeding. In contrast, fat-specific transgenic expression of Nrg4 lowered blood glucose and lipids and reduced liver fat content. The studies described herein established Nrg4 as a novel fat-derived hormone that serves a beneficial role in maintaining metabolic homeostasis. As such, therapeutic targeting of Nrg4 provides a new avenue for treating, e.g., type 2 diabetes, hyperlipidemia, and NAFLD.

Methods provided herein include those wherein the Nrg4 to be administered is an Nrg4 variant at least 45% identical, at least 50% identical, at least 55% identical, at least 60% identical, at least 65% identical, at least 70% identical, at least 75% identical, at least 80% identical, at least 85% identical, at least 90% identical, at least 95% identical, at least 96% identical, at least 97% identical, at least 98% identical, or at least 99% identical to SEQ ID NO: 1.

Nrg4 variants of the invention may comprise conservative substitutions of native amino acids at particular residues. Amino acid residues which share common side-chain properties and are appropriate for generating conservative substitutions are grouped as follows.
(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Also envisioned in this disclosure are methods comprising administration of one or more physiologically active fragments of Nrg4 to treat a condition characterized by insufficient levels or activity of Nrg4. Nrg4 fragments include, but are not limited to, an Nrg4 fragment that lacks the first 4 residues of SEQ ID NO: 1, a fragment that comprises or consists of amino acid residues 5 through 46, 5 through 55, 5 through 62, 1 through 46, 1 through 55, 1 through 52, 1 through 53, 4 through 52, 4 through 53, or 1 through 62 of SEQ ID NO: 1. A person of skill in the art can readily screen for active fragments by screening for activity in a relevant biological assay. In various embodiments, an Nrg4 fragment comprises or consists of amino acid residues x to y, wherein x is 1, 2, 3, 4, 5, 6, 7, 8, 9, 10, 11, 12, 13, 14, 15, 16, 17, 18, 19, 20, 21, 22, 23, 24, or 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 and y is 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, or 115.

An Nrg4, an Nrg4 variant, or a biologically active fragment thereof for use in a method provided is derived from any method known in the art. For example, the Nrg4 in one aspect is derived from cells that express the endogenous Nrg4. Alternatively, the source of the Nrg4, variant, or fragment thereof is derived from cells that are transformed with a nucleic acid vector that encodes Nrg4 or a precursor thereof, and are in various aspects mammalian cells, bacterial cells, yeast cells, insect cells, whole organisms, or other cells that are a useful source recombinant protein.

The N-terminal fragment of Nrg4 (amino acid 1 through approximately amino acid 52 of Nrg4) contains the EGF-like domain and is capable of binding to its receptors on hepatocytes. Synthetic peptides or recombinant Nrg4 produced and purified from mammalian cells (Chinese Hamster Ovary, CHO, for example) may be used to lower blood glucose levels. Chronic treatments with Nrg4 may lower hepatic fat content, similar to the effects elicited by transgenic Nrg4 expression. The synthetic peptides may be modified with N-terminal acetylation, C-terminal amidation, acylation, glycosylation, and PEGylation, among others, to further improve pharmacokinetic profiles. In addition, smaller peptides that retain the biological activities of Nrg4 may be used.

For recombinant production of an Nrg4 protein, isolated DNA and/or recombinant vectors that encode a recombinant Nrg4 protein and control sequences that direct protein expression in bacterial, mammalian or insect cells are provided. In some cases it is desirable that the recombinant Nrg4 coding sequence be fused with an additional amino acid sequence that can, without limitation, facilitate recombinant protein purification. For example, in one aspect, expressed Nrg4 protein is expressed as a fusion protein that includes one or more histidine tags, glutathione S-transferase (GST) sequences, maltose binding protein (MBP) sequences, Flag sequences and/or myc tagged RGT sequences. These additional sequences which aid in purification of the recombinant protein are optionally removed by protease cleavage.

Compounds Capable of Modulating Nrg4 Activity or Expression

Compounds modulating Nrg4 expression (i.e., Nrg4 modulators) are also envisioned to be within the scope of the disclosure. Because Nrg4 expression is severely depressed in obesity, it is likely that compounds or treatments that restore Nrg4 expression in adipocytes may be used to generate therapeutic benefits. It is demonstrated herein that Nrg4 expression is inhibited by inflammatory signals, such as TNFα. As such, anti-inflammatory compounds that restore Nrg4 levels in adipocytes are considered to be within the scope of the disclosure.

Compounds modulating Nrg4 shedding/activation (i.e., Nrg4 modulators) are also envisioned to be within the scope of the disclosure. Nrg4 is synthesized as a precursor transmembrane protein that undergoes proteolytic cleavage and shedding, or release of the Nrg4 soluble, extracellular domain from the membrane-bound protein. The release of soluble Nrg4 into the tissue and circulation is important for activating Nrg4. The identity of exact protease(s) that cleaves Nrg4 remains unknown. Despite this uncertainty, compounds that activate the shedding event and increase the release of active Nrg4 may be screened for and used to achieve similar metabolic benefits as administered Nrg4.

Compounds modulating Nrg4 turnover (i.e., Nrg4 modulators) are also envisioned to be within the scope of the disclosure. Many hormones undergo rapid turnover in circulation. Compounds that block the proteolytic degradation of Nrg4 may increase the concentration of Nrg4 in plasma and achieve metabolic benefits.

Compounds modulating Nrg4 receptor binding and signaling (i.e., Nrg4 modulators) are also envisioned to be within the scope of the disclosure. Additional compounds that improve the binding of Nrg4 to its receptors and augment downstream signaling events may be used to prolong and/or enhance Nrg4 action in target cells.

Conditions Treated by Administration of Nrg4

Methods provided are utilized for the treatment of any condition that can be alleviated by administration of Nrg4, an Nrg4 variant, or a biologically active fragment thereof. In some aspects of methods provided, the condition is a metabolic disorder. Exemplary metabolic disorders include, but are not limited to, type 2 diabetes, hyperglycemia, hyperinsulinemia, insulin resistance, and obesity. In other aspects, the condition is non-alcoholic fatty liver disease (NAFLD), steatohepatitis, hyperlipidemia, dyslipidemia, hypercholesterolemia, non-familial hypercholesterolemia, familial hypercholesterolemia, heterozygous familial hypercholesterolemia, homozygous familial hypercholesterolemia, mixed dyslipidemia, atherosclerosis, early onset coronary heart disease, dyslipidemia, hypertriglyceridemia, hyperfattyacidemia, and cirrhosis. Methods also include those wherein administration of Nrg4, an Nrg4 variant, or a biologically active fragment thereof is to treat disorders or conditions characterized by elevated lipid levels, such lipids including LDL-C, ApoB, VLDL-C, IDL-C, non-HDL-C, Lp(a), serum triglyceride, liver triglyceride, Ox-LDL-C, small LDL particles, small VLDL, phospholipids, and oxidized phospholipids.

In some embodiments, the condition that can be alleviated by administration of Nrg4, an Nrg4 variant, or a biologically active fragment thereof is characterized by reduced expression of NRG4 in adipose tissue compared to expression of NRG4 in adipose tissue from a healthy patient. The adipose tissue can be brown adipose tissue or white adipose tissue.

"Reduced expression of NRG4" indicative of a condition treatable by administration of Nrg4, an Nrg4 variant, or a biologically active fragment thereof may be defined as the decreased level of NRG4 expression in samples from individuals known to have the condition over the NRG4 expression in samples from individuals known to be free of the condition. The level of NRG4 expression may be, for example, at least 1.1 fold, 1.2 fold, 1.3 fold, 1.4 fold, 1.5 fold, 1.6 fold, 1.7 fold, 1.8 fold, 1.9 fold, 2.0 fold, 2.1 fold, 2.2 fold, 2.3 fold, 2.4 fold, 2.5 fold, 2.6 fold, 2.7 fold, 2.8 fold, 2.9 fold, 3.0 fold, 3.1 fold, 3.2 fold, 3.3 fold, 3.4 fold, 3.5 fold, 3.6 fold, 3.7 fold, 3.8 fold, 3.9 fold, 4.0 fold, 4.1 fold, 4.2 fold, 4.3 fold, 4.4 fold, 4.5 fold, 4.6 fold, 4.7 fold, 4.8 fold, 4.9 fold, 5.0 fold, 5.1 fold, 5.2 fold, 5.3 fold, 5.4 fold, 5.5 fold, 5.6 fold, 5.7 fold, 5.8 fold, 5.9 fold, or 6.0 fold lower in a sample from an individual with the condition.

In some embodiments, the condition that can be alleviated by administration of Nrg4, an Nrg4 variant, or a biologically active fragment thereof is aberrant communication between adipocytes and body tissues.

Without wishing to be bound by theory, administered Nrg4, Nrg4 variant, or biologically active fragment thereof negatively regulates the expression of genes involved in de novo lipogenesis. This downregulation of hepatic lipogenesis likely underlies the beneficial metabolic effects of Nrg4.

Compositions and Formulations

The optimal Nrg4 or Nrg4 modulator formulation will be determined by one of skill in the art depending on the route of administration and the desired dosage. Such formulations may influence the physical state, stability, rate of in vivo release and rate of in vivo clearance of the administered agents.

Besides those representative Nrg4 or Nrg4 modulator dosage forms described herein, pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey.

Pharmaceutical compositions comprising Nrg4 or an Nrg4 modulator for use in accordance with the present invention are formulated in a conventional manner using one or more physiologically acceptable carriers comprising excipients and auxiliaries which facilitate processing of a therapeutic composition into preparations which can be used pharmaceutically. These pharmaceutical compositions may be manufactured in a manner that is itself known, e.g., by means of conventional mixing, dissolving, granulating, dragee-making, levigating, emulsifying, encapsulating, entrapping or lyophilizing processes. Proper formulation is dependent upon the route of administration chosen.

When a therapeutically effective amount of an Nrg4 or Nrg4 modulator composition is administered by e.g., intradermal, cutaneous or subcutaneous injection, the composition is, in one aspect, in the form of a pyrogen-free, parenterally acceptable aqueous solution. The preparation of such parenterally acceptable protein or polynucleotide solutions, having due regard to pH, isotonicity, stability, and the like, is within the skill in the art. A composition optionally contains, in addition to Nrg4, Nrg4 modulator or other active ingredient of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The Nrg4 or Nrg4 modulator composition, in another aspect, also contains stabilizers, preservatives, buffers, antioxidants, or other additives known to those of skill in the art. The agents of the invention are formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

The Nrg4 or Nrg4 modulator formulations are, in certain aspects, designed to be short-acting, fast-releasing, long-acting, or sustained-releasing as described below. Thus, one type of pharmaceutical formulations is formulated for controlled release or for slow release. The instant Nrg4 or Nrg4 modulator compositions, in other aspects, comprise, for example, micelles or liposomes, or some other encapsulated form, or may be administered in an extended release form to provide a prolonged storage and/or delivery effect. Therefore, the pharmaceutical Nrg4 or Nrg4 modulator formulations are optionally compressed into pellets or cylinders and implanted intramuscularly or subcutaneously as depot injections or as implants such as stents. Such implants may employ known inert materials such as silicones and biodegradable polymers.

For oral administration, the compositions can be formulated readily by combining the active compounds with pharmaceutically acceptable carriers well known in the art. Such carriers enable the compounds of the invention to be formulated as tablets, pills, dragees, powders, capsules, liquids, solutions, gels, syrups, slurries, suspensions and the like, for oral ingestion by a patient to be treated.

For administration by inhalation, the compositions for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas.

Compositions comprising Nrg4 or an Nrg4 modulator for parenteral administration include aqueous solutions of the compositions in water-soluble form. Optionally, the suspension may also contain suitable stabilizers or agents which increase the solubility of the compositions to allow for the preparation of highly concentrated solutions. Alternatively, the active ingredient may be in powder form for constitution with a suitable vehicle, e.g., sterile pyrogen-free water, before use.

The compositions may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compositions may be formulated with suitable polymeric or hydrophobic materials (for example as an emulsion in an acceptable oil) or ion exchange resins, or as sparingly soluble derivatives, for example, as a sparingly soluble salt.

The compositions also may comprise suitable solid or gel phase carriers or excipients.

The compositions of the invention may be in the form of a complex of the protein(s) or other active ingredient of present invention along with protein or peptide antigens.

The compositions may include a matrix capable of delivering the protein-containing or other active ingredient-containing composition to the site of tissue damage, providing a structure for the developing bone and cartilage and optimally capable of being resorbed into the body. Such matrices may be formed of materials presently in use for other implanted medical applications. The choice of matrix material is based on biocompatibility, biodegradability, mechanical properties, cosmetic appearance and interface properties.

The composition may further contain other agents which either enhance the activity of the protein or other active ingredient or complement its activity or use in treatment. Such additional factors and/or agents may be included in the pharmaceutical composition to produce a synergistic effect with protein or other active ingredient of the invention, or to minimize side effects.

Techniques for formulation and administration of the therapeutic compositions of the instant application may be found in "Remington's Pharmaceutical Sciences," Mack Publishing Co., Easton, Pa., latest edition. When applied to an individual active ingredient, administered alone, a therapeutically effective dose refers to that ingredient alone. When applied to a combination, a therapeutically effective dose refers to combined amounts of the active ingredients that result in the therapeutic effect, whether administered in combination, serially or simultaneously.

Administration

Administration of Nrg4 or an Nrg4 modulator according to the methods provided will be via any route. Conventional routes of administration, e.g., parenterally, subcutaneous, intravenous, intradermal, intramuscular, intramammary, intraperitoneal, intrathecal, intraocular, retrobulbar, intrapulmonary, intratracheal instillation, bronchial instillation, aerosol, sublingual, oral, nasal, anal, vaginal, or transdermal delivery, or by surgical implantation at a particular site are contemplated. Specifically contemplated are methods including intravenous administration.

Treatment in a method provided, in various aspects, consists of a single dose or a plurality of doses over a period of time. Administration of Nrg4 or an Nrg4 modulator is systemic or local, and may comprise a single site injection or infusion of a therapeutically-effective amount of the Nrg4 protein composition. Alternatively, it is contemplated that the therapeutic Nrg4 or Nrg4 modulator composition is delivered to the patient at multiple sites. Multiple administrations are rendered simultaneously or administered over a period of time. Also contemplated is additional therapy wherein Nrg4 or an Nrg4 modulator is administered on a period basis, for example, daily, weekly, or monthly.

In certain embodiments, parenteral administration of the therapeutic compounds is carried out with an initial bolus followed by continuous infusion to maintain therapeutic circulating levels of drug product. Those of ordinary skill in the art will readily optimize effective dosages and administration regimens as determined by good medical practice and the clinical condition of the individual patient. Methods provided include those wherein the Nrg4 is administered orally and by injection. In methods wherein the Nrg4 or Nrg4 modulator is injected, the injection is intravenous or subcutaneous. In certain aspects, injection is with a depot forming composition, and in embodiments including depot formation, the depot forming composition is administered by implanting a suitable delivery device in the patient. In one aspect, the delivery device is implanted subcutaneously, and in certain aspects, the delivery device is a pump.

The frequency of dosing will depend on the pharmacokinetic parameters of the Nrg4 and the routes of administration. Depending on the route of administration, a suitable dose is calculated according to body weight, body surface areas or organ size. The availability of animal models is particularly useful in facilitating a determination of appropriate dosages of a given therapeutic.

Further refinement of the calculations necessary to determine the appropriate treatment dose is routinely made by those of ordinary skill in the art without undue experimentation. The final dosage regimen will be determined by the attending physician, considering factors which modify the action of the Nrg4 or Nrg4 modulator, e.g., the specific activity, the responsiveness of the patient, the age, condition, body weight, sex and diet of the patient, the severity of any condition, time of administration, kind of concurrent treatment, if any, frequency of treatment, and the nature of the effect desired, and other clinical factors. As studies are conducted, further information will emerge regarding appropriate dosage levels and duration of treatment for specific diseases and conditions.

In certain embodiments, the Nrg4 or Nrg4 modulator is administered alone, in other embodiments the Nrg4 or Nrg4 modulator is administered in conjunction with other therapeutics directed to the target condition or directed to other symptoms thereof. Dosage levels of the order from about 0.01 mg to 30 mg per kilogram of body weight per day, for example from about 0.1 mg to 10 mg/kg.

Unit dosages of a Nrg4 or Nrg4 modulator are also provided. "Unit dose" is defined as a discrete amount of a therapeutic composition dispersed in a suitable carrier.

It will be appreciated that the Nrg4 or Nrg4 modulator and treatment methods provided are useful in fields of human medicine and veterinary medicine. Thus, the subject to be treated is a mammal, such as a human or other mammalian animal. For veterinary purposes, subjects include for example, farm animals including cows, sheep, pigs, horses and goats, companion animals such as dogs and cats, exotic and/or zoo animals, laboratory animals including mice rats, rabbits, guinea pigs and hamsters; and poultry such as chickens, turkeys, ducks and geese. The patient being treated is of any age, for example, between the ages of 10-50 years, age 20 or less, or age 10 or less.

In addition, it is contemplated that the Nrg4 or Nrg4 modulator of the present invention is used in combination with any present treatments for non-alcoholic fatty liver disease (NAFLD), steatohepatitis, type II diabetes, hyperglycemia, hyperlipidemia, dyslipidemia, obesity, hyperinsulinemia, insulin resistance, hypercholesterolemia, non-familial hypercholesterolemia, familial hypercholesterolemia, heterozygous familial hypercholesterolemia, homozygous familial hypercholesterolemia, mixed dyslipidemia, atherosclerosis, early onset coronary heart disease, dyslipidemia, hypertriglyceridemia, hyperfattyacidemia, or cirrhosis. For example, in certain embodiments, it is contemplated that the methods of the invention are useful in combination with known metabolic disorder, cardiovascular disorder and/or elevated lipid disorder therapy. Compositions comprising a Nrg4, variant, or a fragment, or Nrg4 modulator are administered before, after or during such therapy.

Combination Therapy

In order to increase the effectiveness of a treatment with the Nrg4 or Nrg4 modulator compositions provided, it is in one aspect desirable to combine these compositions with other therapies effective in the treatment of specific diseases or conditions.

In some cases, the compositions of the present invention precede or follow the other agent treatment by intervals ranging from minutes to weeks. It is contemplated that one administers both modalities within about 12-24 h of each other or within about 6-12 h of each other. In some situations, it is desirable to extend the time period for treatment significantly, where several days (2, 3, 4, 5, 6 or 7) to several weeks (1, 2, 3, 4, 5, 6, 7 or 8) lapse between the respective administrations.

In certain specific instances, Nrg4 or Nrg4 modulator compositions are administered in combination with a second agent to prevent or treat a metabolic disorder or to prevent or treat a cardiovascular disease. For examples, agents that are useful in combination therapies include, but are not limited to, blood sugar-lowering agents (i.e., agents that lower blood sugar) or lipid-lowering agents (i.e., agents that reduce lipid levels).

Blood Sugar-Lowering Agents

Currently, there are various pharmacological approaches for the treatment of Type 2 diabetes. They act via different modes of action: 1) sulfonylureas (e.g., glimepiride, glisentide, sulfonylurea, AY31637) essentially stimulate insulin secretion; 2) biguanides (e.g., metformin) act by promoting glucose utilization, reducing hepatic glucose production and diminishing intestinal glucose output; 3) alpha-glucosidase inhibitors (e.g., acarbose, miglitol) slow down carbohydrate digestion and consequently absorption from the gut and reduce postprandial hyperglycemia; 4) thiazol-idinediones (e.g., troglitazone, pioglitazone, rosiglitazone, glipizide, balaglitazone, rivoglitazone, netoglitazone, troglitazone, englitazone, AD 5075, T 174, YM 268, R 102380, NC 2100, NIP 223, NIP 221, MK 0767, ciglitazone, adaglitazone, CLX 0921, darglitazone, CP 92768, BM 152054) enhance insulin action, thus promoting glucose utilization in peripheral tissues; 5) glucagon-like-peptides and agonists (e.g. exendin) or stabilizers thereof (e.g. DPP4 inhibitors, such as sitagliptin) potentiate glucose-stimulated insulin secretion; and 6) insulin or analogues thereof (e.g. LANTUS®) stimulate tissue glucose utilization and inhibits hepatic glucose output. The above mentioned pharmacological approaches may be utilized individually or in combination therapy.

Lipid-Lowering Agents

The term "lipid-lowering agent" refers to a pharmaceutical agent provided to a individual to achieve a lowering of lipids in the individual. For example, in certain embodiments, a lipid-lowering agent is provided to an individual to reduce one or more of LDL-C, ApoB, VLDL-C, IDL-C, non-HDL-C, Lp(a), serum triglyceride, liver triglyceride, Ox-LDL-C, small LDL particles, small VLDL, phospholipids, and oxidized phospholipids. Ideally, administration of a lipid-lowering agent leads to a reduction of one or more serum lipids in an individual over time.

In certain such embodiments, lipid-lowering pharmaceutical agents that may be co-administered with a pharmaceutical composition of the present invention include, but are not limited to atorvastatin, simvastatin, rosuvastatin, pravastatin, fluvastatin, ezetimibe, bezafibrate, ciprofibrate, clofibrate, gemfibrozil, and fenofibrate. In certain such embodiments, the lipid-lowering agent is administered prior to administration of a pharmaceutical composition of the present invention. In certain such embodiments, the lipid-lowering agent is administered following administration of a pharmaceutical composition of the present invention. In certain such embodiments the lipid-lowering agent is administered at the same time as a pharmaceutical composition of the present invention. In certain such embodiments the dose of a co-administered lipid-lowering agent is the same as the dose that would be administered if the lipid-lowering agent was administered alone. In certain such embodiments the dose of a co-administered lipid-lowering agent is lower than the dose that would be administered if the lipid-lowering agent was administered alone. In certain such embodiments the dose of a co-administered lipid-lowering agent is greater than the dose that would be administered if the lipid-lowering agent was administered alone.

Kits

The present invention also contemplates kits for use in the treatment of a disorder described herein. Such kits include at least a first sterile composition comprising an Nrg4 (SEQ ID NO: 1), an Nrg4 variant, or a biologically active fragment thereof described above in a pharmaceutically acceptable carrier. Another component is optionally a second therapeutic agent for the treatment of the disorder along with suitable container and vehicles for administrations of the therapeutic compositions. The kits optionally comprise solutions or buffers for suspending, diluting or effecting the delivery of the first and second compositions. The kits also optionally comprise catheters, syringes or other delivering devices for the delivery of one or more of the compositions used in the methods of the invention. In another aspect, the kits optionally further comprise instructions containing administration protocols for the therapeutic regimens.

Methods of Diagnosing Conditions Characterized by Nrg4 Deficiency

The present disclosure also contemplates methods of diagnosing a metabolic disorder selected from the group consisting of non-alcoholic fatty liver disease (NAFLD), steatohepatitis, type II diabetes, hyperglycemia, hyperlipidemia, dyslipidemia, obesity, hyperinsulinemia, insulin resistance, hypercholesterolemia, non-familial hypercholesterolemia, familial hypercholesterolemia, heterozygous familial hypercholesterolemia, homozygous familial hypercholesterolemia, mixed dyslipidemia, atherosclerosis, early onset coronary heart disease, dyslipidemia, hypertriglyceridemia, hyperfattyacidemia, and cirrhosis in a patient comprising determining Nrg4 levels in a sample from the patient suspected of suffering from the condition.

It will be appreciated that determination of the level of Nrg4 in a patient sample will be useful in determining how to manage the condition in the patient. For example, since reduced levels of Nrg4 are associated with metabolic disorders and liver diseases, the clinician may use the information concerning the levels of Nrg4 to facilitate decision making regarding treatment of the patient. Thus, if the level of Nrg4 is indicative of an early stage of one of the above-mentioned conditions, appropriate treatment regimens may be prescribed.

The level of Nrg4 which is indicative of the metabolic disorder may be defined as the decreased level of Nrg4 present in samples from individuals known to have the disorder over the Nrg4 level in samples from individuals known to be free of the disorder. The level of Nrg4 may be, for example, at least 1.1 fold, 1.2 fold, 1.3 fold, 1.4 fold, 1.5 fold, 1.6 fold, 1.7 fold, 1.8 fold, 1.9 fold, 2.0 fold, 2.1 fold, 2.2 fold, 2.3 fold, 2.4 fold, 2.5 fold, 2.6 fold, 2.7 fold, 2.8 fold, 2.9 fold, 3.0 fold, 3.1 fold, 3.2 fold, 3.3 fold, 3.4 fold, 3.5 fold, 3.6 fold, 3.7 fold, 3.8 fold, 3.9 fold, 4.0 fold, 4.1 fold, 4.2 fold, 4.3 fold, 4.4 fold, 4.5 fold, 4.6 fold, 4.7 fold, 4.8 fold, 4.9 fold, 5.0 fold, 5.1 fold, 5.2 fold, 5.3 fold, 5.4 fold, 5.5 fold, 5.6 fold, 5.7 fold, 5.8 fold, 5.9 fold, or 6.0 fold lower in a sample from an individual with the disorder.

It will be appreciated that the methods of the invention include methods which aid diagnosis and methods of prognosis. It will also be appreciated that the methods of the invention are useful to the physician in determining a course of management or treatment of the patient.

The NRG4 markers identified using the methods provided are, in one aspect, used to evaluate treatment efficacy (e.g., amelioration of one or more symptoms of a pathology). Where the amelioration of a condition related to Nrg4 deficiency can be related to an increase in levels of Nrg4, Nrg4 levels in a sample taken from the patient are measured before (for background) and during or after (e.g., at a designated time, periodically or randomly) the course of treatment. Because an increase in Nrg4 levels may be transient, the method is, in one aspect, performed at regular intervals, (e.g., every 6 hours, every 12 hours, every 18 hours, every 24 hours, every 2 days, every 3 days, every 4 days, every 5 days, every 6 days, every 7 days, every 8 days, every 9 days, every 10 days, every 11 days, every 12 days, every 13 days, every 2 weeks, every 3 weeks, every 4 weeks, every 5 weeks, every 6 weeks, every 7 weeks, every 2 months, every 3 months, every 4 months, every 5 months, every 6 months, every 7 months, every 8 months, every 9 months, every 10 months, every 11 months, every year, or more) closely before and after each treatment. Depending on the course of treatment and other clinical variables, clinicians of ordinary skill in the art will be able to determine an appropriate schedule for performing the assay for diagnostic or disease/treatment monitoring purposes.

In various embodiments, the Nrg4 protein is detected and/or quantified in the sample using any of a number of well recognized immunological binding assays (see, e.g., U.S. Pat. Nos. 4,366,241; 4,376,110; 4,517,288; and 4,837,168). For a review of general immunoassays, see also Methods in Cell Biology Volume 37: Antibodies in Cell Biology, Asai, ed. Academic Press, Inc. New York (1993); Basic and Clinical Immunology 7th Edition, Stites & Terr, eds. (1991).

In another embodiment, immunoblot (Western blot) analysis is used to detect and quantify the presence of Nrg4 in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the Nrg4. The anti-Nrg4 antibodies specifically bind to the Nrg4 on the solid support. These antibodies may be directly labeled or alternatively may be subsequently detected using labeled antibodies (e.g., labeled sheep anti-mouse antibodies) that specifically bind to the anti-Nrg4 antibody.

In another embodiment, quantitative assays of Nrg4 are deemed to show a positive result, e.g., elevated or decreased Nrg4 level, when the measured Nrg4 level is greater or less than the level measured or known for a control sample (e.g. either a level known or measured for a normal healthy individual or a "baseline/reference" level determined at a different time for the same individual. In a particularly preferred embodiment, the assay is deemed to show a positive result when the difference between sample and "control" is statistically significant (e.g. at the 85% or greater, preferably at the 90% or greater, more preferably at the 95% or greater and most preferably at the 98% or greater confidence level).

In one embodiment of the disclosure, antibodies immunoprecipitate Nrg4 proteins from solution as well as react with Nrg4 protein on western or immunoblots of polyacrylamide gels. In another embodiment, antibodies detect Nrg4 proteins in stored serum samples.

EXAMPLES

The following examples are provided for illustration and are not in any way to limit the scope of the invention.

Example 1

Nrg4 is an Adipocyte-derived Factor that Targets Hepatocytes

In this example, it is demonstrated using a hormone binding assay, that Nrg4 binds to hepatocytes and lowers blood glucose concentrations following i.p. injections. Metabolic studies in Nrg4 null mice also demonstrated that Nrg4 deficiency exacerbated the development of hyperglycemia and hyperlipidemia following HFD feeding. In addition, mice lacking Nrg4 developed more severe fatty liver. These findings underscore an important role of Nrg4 in the regulation of whole body glucose and lipid metabolism.

Materials and Methods
Generation of Nrg4 Transgenic Mice

Mouse Nrg4 cDNA (including 5'UTR and partial 3'UTR) was TA-cloned into pCR2.1 TOPO vector. AP2 promoter was inserted between HindIII and KpnI on the vector, while human growth hormone polyA was inserted between EcoRV and XbaI. The whole vector was linearized by double digestion with HindIII and ApaI to release the transgenic cassette for microinjecting into C57BL/6J mouse eggs for generating AP2-Nrg4 transgenic pups.

Nrg4 knockout mice were purchased from Mutant Mice Regional Resource Center (MMRRC).

Adipocyte Differentiation and Treatments

SV40 T-large antigen immortalized brown pre-adipocytes were cultured in DMEM with 10% fetal bovine serum (FBS) until 2 days post confluent (count as day 0). Differentiation was induced by adding a cocktail containing 0.5 mM IBMX, 125 µM Indomethacin, 1 µM dexamethasone to a differentiation maintenance DMEM containing 10% FBS, 20 nM insulin and 1 nM T3. Two to three days after induction, cells were cultured in the maintenance media alone. Total RNA was isolated at different days during brown adipocyte differentiation for gene expression analysis.

3T3-L1 preadipocytes were cultured in DMEM with 10% bovine growth serum (BGS) until 2 days post confluent (count as day 0). Differentiation was induced by adding a cocktail containing 0.5 mM IBMX, 1 µM dexamethasone and 1 µg/mL insulin to DMEM supplemented with 10% FBS. Three days after induction, cells were cultured in DMEM containing 10% FBS plus 1 µg/mL of insulin for another 2 days followed by maintenance in DMEM supplemented with 10% FBS. For TNFα treatment, 10 ng/mL of TNFα were added to mature (day 8) 3T3-L1 adipocytes cultured in 10% FBS DMEM for six hours respectively before RNA isolation. For IL-1β treatment, 40 ng/mL of IL-1β were added to mature (day 8) 3T3-L1 adipocytes cultured in 10% FBS DMEM for six hours before RNA isolation.

Nrg4 Binding Assay 293T cells were transfected with vectors expressing SEAP or SEAP-Nrg4$^{N62}$. 24 hours after transfection, cells were switched to serum-free media for additional 2 days before the media were collected and concentrated using Centricon. Briefly, frozen tissue slices were incubated with SEAP or SEAP-Nrg4$^{N62}$ conditioned media for 45 min at room temperature before they were washed four times in 0.1% tween-20 containing PBS and fixed in a solution containing 20 mM HEPES (pH 7.4), 60% acetone, and 3% formaldehyde. After inactivating endogenous alkaline phosphatase at 65° C. for 30 min, the enzymatic activity derived from the fusion protein was detected using NBT/BCIP substrate. For competition binding, frozen tissue slices were pre-incubated with 4 µg/µL GST or GST-Nrg4$^{N62}$ for 30 min, before co-incubation with SEAP-Nrg4$^{N62}$ conditioned media for another one hour.

Results

Nrg4 is a member of the neuregulin family of extracellular signaling ligands that also includes Nrg1, Nrg2, and Nrg3. The major coding isoform of Nrg4 is predicted to encode a protein of 115 a.a., which contains a single EGF-like domain with three characteristic disulfide bonds between Cys9-Cys23, Cys17-Cys34, and Cys36-Cys45, a putative N-linked glycosylation site, and a transmembrane domain (FIG. 1) Like other neuregulins, Nrg4 is synthesized as a transmembrane protein and undergoes proteolytic cleavage that liberates the extracellular EGF-like peptide for receptor binding and signal transduction. The identity of proteases responsible for the shedding of Nrg4 is currently unknown, but it is likely to be matrix metalloproteases. Nrg4 is highly conserved between mouse and human with over 90% amino acid sequence identity in the EGF-like domain (amino acid 1 to approximately amino acid 52 of Nrg4, FIG. 1).

Nrg4 expression has been reported in pancreas, mammary epithelial cells, prostate cancers, and lymphoma cell lines. However, Nrg4 pre-mRNA transcript undergoes complex alternative splicing and generates a number of splicing isoforms that appear to lack protein-coding potential. In addition, the specificity of Nrg4 antibodies used in previous immunohistochemical studies remains uncertain. As such, the exact profile of Nrg4 expression and its regulation have not been conclusively established. A Taqman quantitative PCR (qPCR) method was developed herein that specifically detects the coding isoform of Nrg4. Nrg4 mRNA was found to be abundantly expressed in brown adipose tissue (BAT) and white adipose tissue (WAT), but not in other tissues examined, including kidney, skeletal muscle, brain, testis, small intestine, liver, heart, spleen, lung, and pancreas (FIG. 2A). The restriction of Nrg4 expression to adipose tissues suggest that, under normal physiological conditions, Nrg4 may serve as a ligand that mediates the communication between adipocytes and other tissues in the body. Nrg4 expression was also examined to determine if it is regulated during brown and white adipocyte differentiation. Similar to UCP1, a marker for brown adipocytes, Nrg4 mRNA expression is highly induced during brown adipocyte differentiation (FIG. 2B). Nrg4 mRNA levels also increased significantly during the differentiation of 3T3-L1 white adipocytes (FIG. 2B).

Brown fat plays an important role in adaptive thermogenesis in response to cold exposure in rodents. As Nrg4 is highly expressed in brown adipose tissue, its potential role in cold-induced thermogenesis was evaluated. Wild type and Nrg4 deficient mice were exposed to cold temperature (4° C.) and rectal temperature was measured at different time points. Core body temperature in these two groups of mice was nearly indistinguishable during cold exposure, suggesting that Nrg4 is not required for defense against acute cold stress (FIG. 3A). The histological appearance of brown fat was similar between WT and KO groups (FIG. 3B). Cold-inducible expression of brown fat genes, such as UCP1 and deiodinase 2 (DIO2), was also similar (FIG. 3C). Interestingly, plasma triglyceride (TG) concentration was higher, whereas plasma non-esterified fatty acids and ketone (β-hydroxybutyrate) levels were lower in Nrg4-deficient mice (FIG. 3D). These observations suggest that, despite its adipose-specific expression, Nrg4 likely targets other cell types in the body.

To identify tissue targets for Nrg4 binding and action, a fusion protein was generated between secreted alkaline phosphatase (SEAP) and the N-terminal 62 amino acids of Nrg4 (SEAP-Nrg4$^{N62}$) and binding assays were performed as previously described. This fragment of Nrg4 contains the EGF-like domain and is predicted to be competent in initiating signal transduction. Conditioned media was collected from HEK 293T cells transiently transfected with SEAP or SEAP-Nrg4$^{N62}$ plasmids and concentrated using a Centricon spin column. Binding assays were performed on tissue sections followed by extensive washing, fixation, heat inactivation, and incubation with alkaline phosphatase substrates (BCIP/NBT). Only background signals were detected on brown fat, heart, skeletal muscle, and spleen for both SEAP and SEAP-Nrg4$^{N62}$ (FIG. 4A). In contrast, strong binding of SEAP-Nrg4$^{N62}$ to hepatocytes was observed (FIG. 4B). Further, the presence of excess GST-Nrg4$^{N62}$, but not GST, abolished the binding of SEAP-Nrg4$^{N62}$ to hepatocytes, suggesting that the putative Nrg4 binding sites on hepatocytes are limited and saturable (FIG. 4C).

Example 2

Adipocyte Nrg4 Expression is Down-regulated in Obesity

In this example, using a highly sensitive and specific Taqman quantitative PCR assay, it was discovered that Nrg4 was abundantly expressed in brown and white adipose tissues. Very little mRNA expression was detected in other tissues. The expression of Nrg4 was highly inducible during adipocyte differentiation. This expression profile suggests that Nrg4 may serve an unappreciated role in mediating the crosstalk between adipose tissues and other metabolic tissues. Nrg4 mRNA expression was markedly reduced in adipose tissues from diet-induced and genetic obese mice. As such, obesity is associated with a potential deficit of Nrg4 expression and action.

Materials and Methods

Metabolic Measurements

Plasma glycerol/triglyceride, ketone/cholesterol and non-esterified fatty acid concentrations were measured using commercial assay kits (Sigma, Stanbio Laboratory, Wako Diagnostics respectively).

Gene Expression Analysis

Total RNA from white adipose tissue was extracted using a commercial kit from Invitrogen. RNAs from other tissues and cultured cells was extracted using TRIzol method. For quantitative real-time PCR (qPCR) analysis, equal amount of RNA was reverse-transcribed using MMLV-RT followed by quantitative PCR reactions using SYBR Green (Life Technologies). Relative abundance of mRNA was normalized to ribosomal protein 36B4.

For detecting the coding isoform of Nrg4 using Taqman PCR, a sense primer encompassing the junction of exon3 and exon6 (5' CCCAGCCCATTCTGTAGGTG 3' (SEQ ID NO: 3)), an anti-sense primer in exon6 (5'ACCAC-GAAAGCTG-CCGACAG 3' (SEQ ID NO: 4)), and a taqman probe in exon6 but between sense and anti-sense primers (5' 6-FAM-CGGAGCACGCTGCGAAGAGGTT-BHQ 3' (SEQ ID NO: 5)) were generated. Taqman PCR was carried out using the Taqman Universal PCR Master Mix system from ABI, relative abundance of the Nrg4 coding isoform was normalized to ribosomal protein 36B4.

Results

To determine whether Nrg4 expression is dysregulated in obesity, qPCR analyses on total RNA isolated from adipose tissues from mice fed standard chow (lean) or a high-fat diet (HFD) containing 60% fat-derived calorie (obese) were performed. As expected, the expression of TNFα, an inflammatory cytokine, was elevated in epididymal white fat from HFD-fed mice (FIG. 5A). While Nrg4 expression in brown fat was similar between two groups, its mRNA levels were markedly reduced in epididymal white fat in diet-induced obese mice (FIG. 5A and FIG. 15A). Similarly, Nrg4 expression was also significantly reduced in both epididymal white fat and brown fat from leptin or leptin receptor-deficient (ob/ob or db/db) mice, two more severe genetic models of obesity (FIG. 5B and FIG. 15A). Down-regulation of Nrg4 expression occurred specifically in adipocytes (FIG. 5C and FIG. 15B). In fact, Nrg4 mRNA level was very low in the stromal vascular fraction of epididymal white fat. In contrast, the mature adipocyte fraction expressed abundant Nrg4, which was decreased dramatically in obesity. Because pro-inflammatory cytokines have been associated with adipose tissue insulin resistance and metabolic dysregulation, experiments were performed to determine whether pro-inflammatory cytokine signaling modulates Nrg4 expression in cultured adipocytes. Fully differentiated brown and 3T3-L1 adipocytes were treated with vehicle (PBS), TNFα or IL-1β for different periods of time before total RNA was isolated from treated cells for gene expression analysis. Compared to vehicle, TNFα and IL-1β treatment drastically decreased Nrg4 mRNA expression in both brown and white adipocytes (FIG. 5D and FIG. 15C).

The relationship between Nrg4 expression in fats and the severity of obesity was further examined. A group of wild type C57BL/6J male mice was fed with high-fat diet for approximately two months to induce obesity. HFD-fed mice developed obesity of varying severity and had body weight ranging from 30.7 to 51.9 grams. Metabolic parameters were measured in these mice and their association with Nrg4 expression in visceral fats was examined. Nrg4 mRNA expression was inversely correlated with both body weight (R2=0.632) and epididymal white fat weight (R2=0.726) (FIGS. 6A and B). Further, mice with low Nrg4 expression tended to develop more severe hyperglycemia and have higher fat content in the liver. In contrast, high Nrg4 expression in white fat was associated with lower blood glucose and hepatic fat accumulation (FIGS. 6C and D). Together, these studies demonstrate that Nrg4 expression is severely reduced in obesity and strongly suggest that its insufficiency may be linked to the development of obesity-associated metabolic disorders, such as hyperglycemia and fatty liver.

Example 3

Loss of Nrg4 Exacerbates Diet-induced Insulin Resistance, Hepatic Steatosis, and Hypertriglyceridemia To provide proof-of-concept evidence that elevating Nrg4 levels may confer metabolic benefits, fat-specific Nrg4 transgenic mice were generated to rescue the decrease in Nrg4 expression in obesity in this example. In striking contrast to Nrg4 deficiency, Nrg4 transgenic mice had significantly lowered blood glucose and lipid concentrations and reduced fat accumulation in the liver. As such, augmentation of Nrg4 hormonal signaling is predicted to ameliorate the development of metabolic disorders associated with obesity.

To define the extent to which Nrg4 insufficiency contributes to the pathogenesis of metabolic disorders, metabolic parameters were measured in wild type (WT) and Nrg4 knockout (KO) mice following HFD feeding. Nrg4 KO mice are viable, grow normally, and are indistinguishable from WT littermates when fed standard chow. Following HFD-feeding, Nrg4 null mice gained slightly more body weight than control (FIG. 7A). In addition, blood glucose levels were higher in Nrg4 null mice (FIG. 7B). Plasma insulin concentrations were also elevated in mice lacking Nrg4 (FIG. 7B), suggesting that Nrg4 may serve a protective role in maintaining glucose homeostasis, particularly in metabolic stress states such as obesity. Plasma triglyceride levels were higher in Nrg4 null mice, whereas the concentrations of β-hydroxybutyrate, a major constituent of ketone bodies, were lower in the null group (FIG. 7C). Because ketone bodies are products of hepatic fatty acid β-oxidation, these results are consistent with Nrg4 binding to hepatocytes and a potential role of this factor in regulating hepatic lipid metabolism. To further test this possibility, hepatic fat content was measured. Compared to control, Nrg4 null mice have elevated triglyceride deposition in the liver following HFD feeding (FIG. 8A). Histological staining indicated that there was a marked increase of lipid accumulation in Nrg4 KO hepatocytes. In contrast, the histological appearance of adipose tissues remained similar between two groups (FIG. 8B).

It can be concluded from these studies that loss of Nrg4 signaling exacerbates diet-induced metabolic dysregulation, particularly glycemic control, the progression of fatty liver, and plasma triglyceride homeostasis.

Example 4

Transgenic Expression of Nrg4 in Adipose Tissues Ameliorates Diet-induced Metabolic Dysregulation This example demonstrates that at the mechanistic level, Nrg4 signals through modulating metabolic gene expression. Nrg4 negatively regulates the expression of genes involved in de novo lipogenesis. This downregulation of hepatic lipogenesis likely underlies the beneficial metabolic effects of Nrg4.

Results

As described above, adipocyte Nrg4 expression was significantly decreased in diet-induced and genetic obesity in mice (FIGS. 5A and B). As such, transgenic overexpression of Nrg4 in adipose tissues may normalize or rescue the deterioration of metabolic homeostasis induced by obesity. Further, administration of recombinant Nrg4 protein may provide therapeutic benefits in treating hyperglycemia, non-alcoholic fatty liver disease, and hyperlipidemia. To test these possibilities, fat-specific Nrg4 transgenic mice under the control of aP2 promoter/enhancer were generated, which has been widely used in directing transgenic expression of genes in adipocytes. Five independent transgenic founders were generated with various levels of transgenic expression of Nrg4 in brown and white adipose tissues. Line #111 was chosen for further studies because Nrg4 transgene was specifically expressed in the adipose tissues to levels slightly above its expression in lean mice. AP2-Nrg4 transgenic mice were indistinguishable from non-transgenic littermates with regard to post-natal growth, physical appearance, and general behavioral characteristics.

To determine whether transgenic expression of Nrg4 protects mice from diet-induced metabolic disorders, control and transgenic mice were fed with high-fat diet. The transgenic group gained slightly less weight than control following 11 weeks of HFD feeding (FIG. 9A). Metabolic measurements indicate that AP2-Nrg4 transgenic mice had lower blood glucose under both fed and fasted conditions (FIG. 9C). In contrast to Nrg4 null mice, which had lower plasma ketone levels, transgenic mice had elevated levels of ketones following overnight starvation (FIG. 9C), suggesting that hepatic fatty acid oxidation and ketogenesis might be enhanced by transgenic expression of Nrg4. Plasma triglyceride concentrations were lower in the transgenic group. Glucose tolerance and insulin tolerance tests indicate that AP2-Nrg4 transgenic mice were more glucose tolerant and insulin sensitive (FIGS. 10A-B). In addition to improved plasma metabolic profile, liver fat accumulation was significantly reduced in transgenic mice (FIGS. 10C-D). Consistently, gene expression analysis showed that liver from the transgenic mice had lower expression of major lipogenic genes. The expression of lipid droplet associated genes such as FSP27 and s3-12 was also significantly lower in transgenic liver (FIG. 11). Taken together, these studies provide genetic evidence that elevating Nrg4 levels may result in desirable effects on glycemic control and achieve significant protection against fatty liver disease.

Proof-of-principle studies were performed to evaluate potential therapeutic effects of recombinant Nrg4 protein. GST and GST-Nrg4$^{N62}$ fusion protein were expressed and purified from bacteria containing relevant expression vectors. Two doses of GST or GST-Nrg4$^{N62}$ were administered intraperitoneally to diet-induced obese mice three hours apart. Plasma and tissue samples were harvested three hours after the second dose for metabolite measurements and gene expression analyses. Plasma glucose concentration was significantly lower in mice treated with GST-Nrg4$^{N62}$ than control. Insulin levels also trended lower following GST-Nrg4$^{N62}$ treatments (FIG. 12), suggesting that the ability of GST-Nrg4$^{N62}$ to lower blood glucose was mediated through mechanisms distinct from working as an insulin secretagogue. In this short-term experiment, significant effects of GST-Nrg4$^{N62}$ on plasma and hepatic lipids were not observed. Interestingly, the expression of key enzymes involved in de novo lipogenesis was significantly reduced by GST-Nrg4$^{N62}$, including SREBP1c and SCD1.

Example 5

Synthetic Nrg4 Peptides

To evaluate therapeutic potential of exogenously administered Nrg4 in treating type 2 diabetes and non-alcoholic fatty liver disease, Nrg4 peptide corresponding to the EGF-like domain (a.a. 1-52) of Nrg4 is synthesized. N-terminal acetylation and C-terminal amidation is introduced to improve the stability of peptide in circulation. The biological activity of this peptide is evaluated in cultured cells and in vivo studies are performed under acute and chronic treatment conditions. For acute experiments, the peptide is delivered via i.p. injection at different doses and plasma and liver metabolite concentrations are measured following the injections. These studies are performed in diet-induced and genetic obese mouse models. Hepatic gene expression is analyzed to investigate the target metabolic pathways involved. For chronic treatments, the peptide is delivered via i.p. injections or osmotic pump system to achieve steady and controlled delivery. Metabolic analyses are performed at different time points following the initiation of treatments. Pharmacokinetic properties are altered to overcome rapid clearance and/or inactivation. To this end, Nrg4 peptides with chemical modification of fatty acyl groups (e.g., palmitylation) are generated. Acylated peptides have been shown to associate with serum albumin and have greatly improved half-life in circulation and bioavailability. Additional chemical modifications, such as PEGylation and glycosylation are also generated.

Example 6

Recombinant Nrg4 Produced in Mammalian Cells

Many biologic therapeutics currently in clinical use are recombinant proteins purified from engineered mammalian cell lines. A plasmid that produces Nrg4 as a polyhistine-tagged secreted protein (His-Nrg4) is constructed. Stably transfected Chinese Hamster Ovary (CHO) cell lines are generated that secrete His-Nrg4 and purify recombinant Nrg4 using affinity matrix. This recombinant protein is expected to contain proper glycosylation and disulfide bonds and have pharmacokinetic profiles similar to native Nrg4. The biological activities of recombinant Nrg4 are evaluated in mice. Additionally, a protocol is established to purify non-tagged Nrg4 from CHO cells for in vivo evaluation of its therapeutic effects in lowering blood glucose and treating non-alcoholic fatty liver disease.

Example 7

Mapping of Amino Acids Important for the Release of the Extracellular Fragment of Nrg4

To map the extracellular cleavage sites of Nrg4, a panel of Alanine mutants was generated on amino acids 51-61, which are located between EGF-like and transmembrane domains. To facilitate detection, full-length wild type and mutant Nrg4 proteins were fused to the C-terminus of secreted alkaline phosphatase (SEAP). The cleavage and secretion of mature Nrg4 are detected by the presence of SEAP-Nrg4 fusion protein in conditioned media (CM) from transiently transfected HEK293 cells. Immunoblotting analysis indicated that SEAP-Nrg4 protein was produced, released, and readily detectable in CM from transfected cells (FIG. 14), indicative of shedding of the Nrg4 extracellular domain. Mutants with a.a.53-54 (53-2A) or a.a.53 (53-A) replaced by Alanine had markedly reduced levels of SEAP-Nrg4 fusion protein detectable in CM, despite similar expression of precursor proteins in total cell lysates. In contrast, Alanine mutants at amino acids 51-52, 54, 55-57, 55-58, 58-59, or 60-61 had modest effects on the release of SEAP-Nrg4 into culture media. These results illustrate that a.a.53 is critical for the cleavage of Nrg4 by proteases and its release into the extracellular space.

Example 8

Nrg4 Deficiency Results in Severe Obesity, Insulin Resistance, Hepatic Fat Accumulation, and Hyperlipidemia After Eating a High-fat Diet Additional studies were carried out to determine the effects of a high-fat diet on a subject having Nrg4 deficiency.
Materials and Methods
Body Composition and Metabolic Cage Studies
Wild type and Nrg4 KO mice were fed standard chow or high-fat diet. Body fat and lean mass were measured using an NMR analyzer (Minispec LF90II, Bruker Optics). Oxygen consumption (VO2), spontaneous motor activity and food intake were measured using the Comprehensive Laboratory Monitoring System (CLAMS, Columbus Instruments), an integrated open-circuit calorimeter equipped with an optical beam activity monitoring device. Mice were individually placed into the sealed chambers (7.9"×4"×5") with free access to food and water. The study was carried out in an experimentation room set at 20-23° C. with 12-12 hours (6:00 PM-6:00 AM) dark-light cycles. The measurements were carried out continuously for 72 hours. During this time, animals were provided with food and water through the equipped feeding and drinking devices located inside the chamber. The amount of food of each animal was monitored through a precision balance attached below the chamber. VO2 in each chamber were sampled sequentially for 5 seconds in 10 minute intervals and the motor activity was recorded every second in X and Z dimensions.
Metabolic Measurements
Plasma concentrations of triglycerides (Sigma) and non-esterified fatty acid (Wako Diagnostics) were measured using commercial assay kits. Liver triglyceride was extracted and measured as previously described. Plasma insulin was measured using an ELISA assay kit (Crystal-Chem). Glucose and insulin tolerance tests were performed.

To define the extent to which Nrg4 insufficiency contributes to the pathogenesis of metabolic disorders, metabolic parameters in wild type (WT) and Nrg4 null mice following HFD feeding (Research Diets, D12492) were measured. Nrg4 KO mice were born at the expected Mendelian ratio. Nrg2 KO mice demonstrated similar food intake, physical activity level and oxygen consumption rate, and gained similar body weight as control when fed standard chow (FIG. 16A). Following HFD-feeding, Nrg4 null mice gained slightly more weight, accompanied by significantly increased adiposity and reduced percent lean body mass. Plasma triglyceride (TAG) levels were higher in Nrg4 null mice (FIG. 16B), whereas the concentrations of β-hydroxybutyrate, a major constituent of ketone bodies, were lower in the null group (FIG. 16C). Because ketone bodies are products of hepatic fatty acid β-oxidation, these results are consistent with Nrg4 binding to hepatocytes. These results also demonstrate a role for Nrg4 in regulating hepatic lipid metabolism.

Hepatic fat content was then measured in Nrg4 KN and WT mice. Nrg4 null mice were found to have elevated triglyceride deposition in the liver following HFD feeding (FIG. 17A). Fat content was increased by approximately 60% in Nrg4 null mouse livers. Histological assessment (H&E staining) revealed that Nrg4 null mice developed more severe hepatic steatosis than control group following HFD feeding, whereas the histology of brown and white adipose tissues appeared similar (FIG. 17B).

Compared to control, fasting blood glucose and fed plasma insulin levels were elevated in the KO group (FIG. 18A). Further, glucose tolerance test (GTT) and insulin tolerance test (ITT) revealed that Nrg4 null mice developed more severe glucose intolerance and insulin resistance than control mice (FIGS. 18B and C). Taken together, these results demonstrate that Nrg4 plays a protective role in maintaining glucose homeostasis, particularly in metabolic stress states such as high-fat induced obesity.

These studies demonstrate that loss of Nrg4 signaling exacerbates diet-induced metabolic dysregulation, particularly glycemic control, the progression of fatty liver, and plasma triglyceride homeostasis.

Example 9

Nrg4 Inhibits the Induction of a Lipogenic Gene Program in the Liver

This example demonstrates that Nrg4 signals through attenuating lipogenic gene expression in the liver. Without being bound by theory, it is thought that this downregulation of hepatic lipogenesis likely underlies the beneficial metabolic effects of Nrg4.

Materials and Methods

Immunoblotting Analyses

Total liver lysates were prepared by homogenizing livers in a lysis buffer containing 50 mM Tris (pH 7.5), 150 mM NaCl, 5 mM NaF, 25 mM β-glycerolphosphate, 1 mM sodium orthovanadate, 10% glycerol, 1% tritonX-100, 1 mM dithiothreitol (DTT), and freshly added protease inhibitors. Liver nuclear extracts were also prepared. Briefly, frozen livers were homogenized using a Dounce homogenizer in ice-cold homogenization buffer containing 0.6% NP40, 150 mM NaCl, 10 mM HEPES (pH=7.9), 1 mM EDTA, and protease inhibitor cocktail. The homogenates were briefly centrifuged at 450 rpm at 4° C. to remove tissue debris. The suspension was transferred to a new tube and centrifuged at 3,000 rpm for 5 min at 4° C. The nuclei pellet was washed with homogenization buffer and resuspended in a low-salt buffer containing 20 mM Tris (pH=7.5), 25% glycerol, 1.5 mM MgCl2, 200 μM EDTA, 20 mM KCl, and protease inhibitors. Nuclear proteins were extracted following the addition of a high-salt buffer (½ volume) containing 20 mM Tris (pH=7.5), 1.5 mM MgCl2, 200 μM EDTA, 1.2 M KCl, and protease inhibitors at 4° C. for 2 hrs. Immunoblotting experiments were performed using specific antibodies against SREBP1 and Chrebp (Santa Cruz Biotechnology), tubulin (Sigma), and Lamin A/C, phospho-ErbB4 and total ErbB4, phospho-AKT (S473) and total AKT, phosphor-AMPK (Thr172) and total AMPK (Cell Signaling).

Hepatocyte Isolation and Treatment

Primary hepatocytes were isolated as by using collagenase type II (Invitrogen, Carlsbad, Calif.) from C57BL/6J mice. Hepatocytes were maintained in DMEM medium containing 10% BGS at 37° C. and 5% $CO_2$. Adenovirus infection was performed on the same day of isolation. After 24 hrs, cells were treated with GST and GST-Nrg4Ex (10 μg/mL) with vehicle (DMSO) or T0901317 (5 μmol/L) for 24 hrs. For signaling, cells were switched to DMEM supplemented with 0.1% BSA for 12 hrs before GST and GST-Nrg4Ex treatment. Recombinant adenoviruses were generated using AdEasy adenoviral vector (Stratagene, Santa Clara, Calif.) as previously described (Li et al., Cell Metabolism 8: 105-117, 2008).

Results

Having established that liver is a major metabolic tissue targeted by Nrg4, experiments were carried out to determine the mechanisms through which Nrg4 modulates hepatic metabolism. Gene expression analysis indicated that mRNA levels of several transcriptional regulators of hepatic metabolism, including PGC-1 , PGC-1 , ChREBP, and SREBP2, were similar between control and KO livers (FIG. 19A). In contrast, mRNA expression of SREBP1c, a key regulator of de novo lipogenesis and triglyceride synthesis, was significantly induced in Nrg4 KO mouse livers. Importantly, protein levels of precursor SREBP1 (pSREBP1) and the cleaved and transcriptionally active isoform of SREBP1 in the nucleus (nSREBP1) were also elevated (FIG. 19B). The levels of phospho-AMPK and phospho-AKT (S473), a substrate of mTOR complex 2, were similar between WT and KO livers.

Quantitative PCR analyses indicated that mRNA expression of several known SREBP1 target genes involved in lipogenesis, including glucose kinase (Gck), acetyl-CoA carboxylase 1 (Acct), cytosolic malic enzyme (Me1), fatty acid synthase (Fasn), stearoyl-CoA desaturase 1 (Scd1), and glycerol kinase (Gyk), was significantly higher in the livers of Nrg4 null mice than control mice (FIG. 19A). The expression of Fsp27, a lipid droplet protein associated with hepatic steatosis, was also elevated. In contrast, the expression of genes involved in fatty acid β-oxidation, gluconeogenesis, and mitochondrial oxidative metabolism was comparable between two groups.

Without being bound by theory, aberrant activation of lipogenesis in Nrg4 null mouse livers may result from direct effects of Nrg4 signaling on the lipogenic gene program. Alternatively, it is possible that increased adiposity, while moderate, may contribute to the disruption of hepatic lipid metabolism in Nrg4 null mice. To distinguish these two possibilities, the effects of Nrg4 on lipogenic gene expression in primary hepatocytes was examined. Cultured hepatocytes were treated with vehicle (DMSO) or T0901317, an agonist for liver-X receptor that potently stimulates Srebp1c and lipogenic gene expression, in the presence of CM containing SEAP or SEAP-Nrg4N62. While basal expression of Srebp1c, Fasn, and Scd1 was comparable, their induction in response to LXR activation was significantly diminished by SEAP-Nrg4N62 (FIG. 20).

Example 10

Transgenic Expression of Nrg4 in Adipose Tissues Ameliorates Diet-induced Metabolic Dysregulation This example demonstrates that elevating Nrg4 levels provides beneficial effects to blood glucose regulation and reduces the severity of fatty liver disease.

As described above, adipocyte Nrg4 expression was significantly decreased in diet-induced and genetic obesity in mice. As such, transgenic overexpression of Nrg4 in adipose tissues may normalize or rescue the deterioration of metabolic homeostasis induced by obesity. Further, administration of recombinant Nrg4 protein may provide therapeutic benefits in treating hyperglycemia, non-alcoholic fatty liver disease, and hyperlipidemia. To test these possibilities, transgenic mice were generated with fat-specific Nrg4 under the control of aP2 promoter/enhancer, which has been widely used in directing transgenic expression of genes in adipocytes. Five independent transgenic founders with various levels of transgenic expression of Nrg4 in brown and white adipose tissues were generated. One particular line (designated internally as #111) was chosen for further studies because the Nrg4 transgene was specifically expressed in adipose tissues at levels slightly above Nrg4 expression in lean mice. AP2-Nrg4 transgenic mice were indistinguishable from non-transgenic littermates with regard to post-natal growth, physical appearance, and general behavioral characteristics.

To determine whether transgenic expression of Nrg4 protects mice from diet-induced metabolic disorders, control and transgenic mice were fed a HFD. The transgenic group gained slightly less weight than the control group following 11 weeks of HFD feeding (FIG. 21A). Body composition analyses revealed that percent fat mass was reduced in the transgenic group, whereas percent lean mass remained largely similar (FIG. 21B). Whole body energy metabolism was then measured using a Comprehensive Lab Animal Monitoring System (CLAMS). While control and transgenic mice had similar food intake, transgenic mice exhibited a significantly elevated oxygen consumption rate (VO2) as normalized to body weight or lean body mass (FIG. 21C). Transgenic mice also appeared to have increased locomotor activity levels as monitored by an infrared bead-breaking device. Transgenic mice had lower plasma TAG concentrations and higher levels of ketones following overnight starvation (FIG. 22A), suggesting that hepatic fatty acid oxidation and ketogenesis might be enhanced by transgenic expression of Nrg4. Total cholesterol levels were also lower in the transgenic group.

In contrast to Nrg4 deficiency, Nrg4 transgenic mice had lower blood glucose levels than control under both fed and fasted conditions (FIG. 22B). Fasting plasma insulin level was also lower in the transgenic group. Glucose tolerance test indicate that Nrg4 transgenic mice had improved glucose tolerance following intraperitoneal challenge of glucose (2 mg/kg) (FIG. 23A). Consistent with improved glucose metabolism, transgenic mice were more responsive to insulin in insulin tolerance tests (FIG. 23B). Histological analyses indicated that transgenic mice developed less severe hepatic steatosis (FIG. 24A), whereas adipose tissue histology was similar between two groups. Consistently, liver triglyceride content was reduced in the transgenic group (FIG. 24B).

Gene expression studies were then carried out to investigate downstream metabolic pathways that responded to transgenic elevation of Nrg4. Levels of SREBP1c mRNA and protein were significantly decreased in transgenic mouse livers (FIGS. 24C and D). The expression levels of hepatic lipogenic genes, including Gck, Ad, Acc1, Me1, Fasn, and Scd1, were accordingly attenuated in response to transgenic expression of Nrg4 in adipose tissues. Fsp27 mRNA expression was also markedly reduced. Taken together, these studies provide genetic evidence that elevating Nrg4 levels results in desirable effects on blood glucose and lipid levels, and provide evidence that Nrg4 overexpression may be beneficial in the treatment of non-alcoholic fatty liver disease.

Example 11

Recombinant Nrg4 Fragments

To evaluate therapeutic potential of exogenously administered Nrg4 in treating type 2 diabetes and non-alcoholic fatty liver disease, a vector expressing recombinant Nrg4 protein (GST-Nrg4) was generated using a bacterial host. Proof-of-principle studies were carried out to evaluate potential therapeutic effects of recombinant Nrg4 protein. GST-Nrg4 fusion protein and GST were expressed and purified from bacteria containing relevant expression vectors. Two doses of GST or GST-Nrg4 per day were administered intraperitoneally to diet-induced obese mice for 5 consecutive days. Plasma and tissue samples were harvested two hours after the last injection for metabolite measurements and gene expression analyses. Plasma glucose and insulin concentrations were lower in mice treated with GST-Nrg4 than in control (FIG. 25). Without being bound by theory, these results indicate that the ability of GST-Nrg4 to lower blood glucose is mediated through mechanisms distinct from working as an insulin secretagogue. The expression of enzymes involved in de novo lipogenesis was significantly reduced by GST-Nrg4, including malic enzyme 1 (ME1) and stearoyl-CoA desaturase 1 (SCD1).

The disclosure has been described in terms of particular embodiments found or proposed to comprise specific modes for the practice of the methods and compositions of the invention described herein. Various modifications and variations of the described invention will be apparent to those skilled in the art without departing from the scope and spirit of the invention. Although the disclosure provides specific embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

REFERENCES

Cohen, J. C., Horton, J. D. & Hobbs, H. H. Human fatty liver disease: old questions and new insights. *Science* 332, 1519-1523 (2011).

James, O. & Day, C. Non-alcoholic steatohepatitis: another disease of affluence. *Lancet* 353, 1634-1636 (1999).

Jornayvaz, F. R., Samuel, V. T. & Shulman, G. I. The role of muscle insulin resistance in the pathogenesis of atherogenic dyslipidemia and nonalcoholic fatty liver disease associated with the metabolic syndrome. *Annu Rev Nutr* 30, 273-290 (2010).

Szczepaniak, L. S., et al. Magnetic resonance spectroscopy to measure hepatic triglyceride content: prevalence of hepatic steatosis in the general population. *Am J Physiol Endocrinol Metab* 288, E462-468 (2005).

Browning, J. D., et al. Prevalence of hepatic steatosis in an urban population in the United States: impact of ethnicity. *Hepatology* 40, 1387-1395 (2004).

Loomba, R., Sirlin, C. B., Schwimmer, J. B. & Lavine, J. E. Advances in pediatric nonalcoholic fatty liver disease. *Hepatology* 50, 1282-1293 (2009).

Chitturi, S., et al. NASH and insulin resistance: Insulin hypersecretion and specific association with the insulin resistance syndrome. *Hepatology* 35, 373-379 (2002).

Schneider, M. R. & Wolf, E. The epidermal growth factor receptor ligands at a glance. *Journal of cellular physiology* 218, 460-466 (2009).

Burgess, A. W. EGFR family: structure physiology signalling and therapeutic targets. *Growth factors* 26, 263-274 (2008).

Falls, D. L. Neuregulins and the neuromuscular system: 10 years of answers and questions. *Journal of neurocytology* 32, 619-647 (2003).

Reiss, K. & Saftig, P. The "a disintegrin and metalloprotease" (ADAM) family of sheddases: physiological and cellular functions. *Seminars in cell & developmental biology* 20, 126-137 (2009).

Blobel, C. P., Carpenter, G. & Freeman, M. The role of protease activity in ErbB biology. *Experimental cell research* 315, 671-682 (2009).

Tang, C. S., et al. Genome-wide copy number analysis uncovers a new HSCR gene: NRG3. *PLoS genetics* 8, e1002687 (2012).

Stefansson, H., et al. Neuregulin 1 and susceptibility to schizophrenia. *American journal of human genetics* 71, 877-892 (2002).

Hayes, N. V., Newsam, R. J., Baines, A. J. & Gullick, W. J. Characterization of the cell membrane-associated products of the Neuregulin 4 gene. *Oncogene* 27, 715-720 (2008).

Harari, D., et al. Neuregulin-4: a novel growth factor that acts through the ErbB-4 receptor tyrosine kinase. *Oncogene* 18, 2681-2689 (1999).

Falls, D. L. Neuregulins: functions, forms, and signaling strategies. *Experimental cell research* 284, 14-30 (2003).

Dunn, M., et al. Co-expression of neuregulins 1, 2, 3 and 4 in human breast cancer. *The Journal of pathology* 203, 672-680 (2004).

Hayes, N. V., et al. Identification and characterization of novel spliced variants of neuregulin 4 in prostate cancer.

*Clinical cancer research: an official journal of the American Association for Cancer Research* 13, 3147-3155 (2007).

Ebi, M., et al. The role of neuregulin4 and HER4 in gastrointestinal malignant lymphoma. *Molecular medicine reports* 4, 1151-1155 (2011).

Muller, H., Dai, G. & Soares, M. J. Placental lactogen-I (PL-I) target tissues identified with an alkaline phosphatase-PL-I fusion protein. *The journal of histochemistry and cytochemistry: official journal of the Histochemistry Society* 46, 737-743 (1998).

Lin, J. & Linzer, D. I. Induction of megakaryocyte differentiation by a novel pregnancy-specific hormone. *The Journal of biological chemistry* 274, 21485-21489 (1999).

What is claimed:

1. A method of treating non-alcoholic fatty liver disease (NAFLD), steatohepatitis, or cirrhosis comprising administering to a patient in need thereof a therapeutically effective amount of a neuregulin 4 (Nrg4) protein comprising the amino acid sequence set forth in SEQ ID NO: 1, an Nrg4 variant comprising at least 80%, 85%, 90%, 95%, or 99% identity to the amino acid sequence set forth in SEQ ID NO: 1, or a biologically active fragment thereof comprising residues 1-46, 1-55, 1-52, 1-53, or 1-62 of SEQ ID NO: 1.

2. The method of claim 1, wherein the patient in need thereof is administered a therapeutically effective amount of the Nrg4 protein comprising the amino acid sequence set forth in SEQ ID NO: 1.

3. The method of claim 1, wherein the patient in need thereof is administered a therapeutically effective amount of the Nrg4 variant comprising at least 80%, 85%, 90%, 95%, or 99% identity to the amino acid sequence set forth in SEQ ID NO: 1.

4. The method of claim 3, wherein the Nrg4 variant comprises at least 80% identity to the amino acid sequence set forth in SEQ ID NO: 1.

5. The method of claim 4, wherein the Nrg4 variant comprises at least 85% identity to the amino acid sequence set forth in SEQ ID NO: 1.

6. The method of claim 5, wherein the Nrg4 variant comprises at least 90% identity to the amino acid sequence set forth in SEQ ID NO: 1.

7. The method of claim 6, wherein the Nrg4 variant comprises at least 95% identity to the amino acid sequence set forth in SEQ ID NO: 1.

8. The method of claim 7, wherein the Nrg4 variant comprises at least 99% identity to the amino acid sequence set forth in SEQ ID NO: 1.

9. The method of claim 1, wherein the patient in need thereof is administered a therapeutically effective amount of a biologically active fragment of the Nrg4 protein comprising residues 1-46, 1-55, 1-52, 1-53, or 1-62 of SEQ ID NO: 1.

10. The method of claim 9, wherein the biologically active fragment comprises residues 1-46 of SEQ ID NO: 1.

11. The method of claim 9, wherein the biologically active fragment comprises residues 1-55 of SEQ ID NO: 1.

12. The method of claim 9, wherein the biologically active fragment comprises residues 1-52 of SEQ ID NO: 1.

13. The method of claim 9, wherein the biologically active fragment comprises residues 1-53 of SEQ ID NO: 1.

14. The method of claim 9, wherein the biologically active fragment comprises residues 1-62 of SEQ ID NO: 1.

* * * * *